US009567317B2

(12) United States Patent
Chiodo et al.

(10) Patent No.: US 9,567,317 B2
(45) Date of Patent: Feb. 14, 2017

(54) MULTICOMPONENT CRYSTALLINE SYSTEM COMPRISING NILOTINIB AND SELECTED CO-CRYSTAL FORMERS

(71) Applicant: BASF SE, Ludwigshafen (DE)

(72) Inventors: Tiziana Chiodo, Mannheim (DE); Andreas Hafner, Gelterkinden (CH); Tobias Hintermann, Therwil (CH); Beate Salvador, Ellerstadt (DE); Martin Szelagiewicz, Basel (CH); Fritz Blatter, Reinach (CH); Eva Roedel, Basel (CH); Marcus Vossen, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/433,147

(22) PCT Filed: Oct. 16, 2013

(86) PCT No.: PCT/EP2013/071580
§ 371 (c)(1),
(2) Date: Apr. 2, 2015

(87) PCT Pub. No.: WO2014/060449
PCT Pub. Date: Apr. 24, 2014

(65) Prior Publication Data
US 2015/0246901 A1    Sep. 3, 2015

Related U.S. Application Data

(60) Provisional application No. 61/715,865, filed on Oct. 19, 2012.

(30) Foreign Application Priority Data

Oct. 19, 2012  (EP) ..................................... 12189264
May 14, 2013  (EP) ..................................... 13167657

(51) Int. Cl.
C07D 401/14    (2006.01)
(52) U.S. Cl.
CPC .................................. C07D 401/14 (2013.01)
(58) Field of Classification Search
CPC combination set(s) only.
See application file for complete search history.

(56) References Cited

U.S. PATENT DOCUMENTS

| 7,169,791 B2 | 1/2007 | Breitenstein et al. |
| 8,716,305 B2 | 5/2014 | Hafner et al. |
| 8,796,481 B2 | 8/2014 | Berens et al. |
| 8,841,316 B2 | 9/2014 | Hafner et al. |
| 2004/0176335 A1 | 9/2004 | Childs |
| 2006/0167015 A1 | 7/2006 | Breitenstein et al. |
| 2007/0093506 A1 | 4/2007 | Breitenstein et al. |
| 2008/0188451 A1 | 8/2008 | Breitenstein et al. |
| 2008/0200487 A1 | 8/2008 | Manley et al. |
| 2008/0269269 A1 | 10/2008 | Manley et al. |
| 2009/0281195 A1 | 11/2009 | Childs |
| 2009/0286821 A1 | 11/2009 | Breitenstein et al. |
| 2011/0218187 A1 | 9/2011 | Breitenstein et al. |
| 2012/0270891 A1 | 10/2012 | Manley et al. |
| 2013/0023548 A1 | 1/2013 | Manley et al. |
| 2013/0158059 A1 | 6/2013 | Piran et al. |
| 2013/0165465 A1 | 6/2013 | Manley et al. |
| 2013/0237553 A1 | 9/2013 | Hafner et al. |
| 2014/0155371 A1 | 6/2014 | Hafner et al. |
| 2014/0205641 A1 | 7/2014 | Sowa et al. |
| 2015/0065347 A1 | 3/2015 | Chiodo et al. |
| 2015/0087657 A1 | 3/2015 | Hafner et al. |
| 2015/0099631 A1 | 4/2015 | Reinhard et al. |
| 2015/0126520 A1 | 5/2015 | Chiodo et al. |
| 2015/0133463 A1 | 5/2015 | Chiodo et al. |
| 2015/0141253 A1 | 5/2015 | Reinhard et al. |

FOREIGN PATENT DOCUMENTS

| WO | WO 2004/005281 A1 | 1/2004 |
| WO | WO 2004/064762 A2 | 8/2004 |
| WO | WO 2007/015870 A2 | 2/2007 |
| WO | WO 2007/015871 A1 | 2/2007 |
| WO | WO 2010/054056 A2 | 5/2010 |
| WO | WO 2010/081443 A2 | 7/2010 |
| WO | WO 2011/086541 A1 | 7/2011 |
| WO | WO 2011/163222 A1 | 12/2011 |
| WO | WO 2012/069394 A1 | 5/2012 |
| WO | WO 2012/143308 A1 | 10/2012 |
| WO | WO 2013/014604 A1 | 1/2013 |
| WO | WO 2013/030777 A1 | 3/2013 |
| WO | WO 2013/084130 A1 | 6/2013 |
| WO | WO 2013/098370 A1 | 7/2013 |
| WO | WO 2013/143927 A1 | 10/2013 |
| WO | WO 2013/174693 A1 | 11/2013 |
| WO | WO 2013/174694 A1 | 11/2013 |
| WO | WO 2013/186726 A2 | 12/2013 |
| WO | WO 2013/189910 A1 | 12/2013 |
| WO | WO 2014/023682 A1 | 2/2014 |

OTHER PUBLICATIONS

International Search Report issued Apr. 7, 2014 in PCT/EP2013/071580 filed Oct. 16, 2013.
Search Report issued Jan. 15, 2013 in EP 12 18 9264.
Scott L. Childs et al: "The Salt-Cocrystal Continuum: The Influence of Crystal Structure on Ionization State", Molecular Pharmaceutics, vol. 4, No. 3, XP002483371, 2007, pp. 323-338.
U.S. Appl. No. 14/415,875, filed Jan. 20, 2015, Hafner, et al.

Primary Examiner — Shirley V Gembeh
(74) Attorney, Agent, or Firm — Oblon, McClelland, Maier & Neustadt, L.L.P.

(57) ABSTRACT

The present invention relates to crystalline materials comprising nilotinib and a carboxylic acid, carboxylic acid ester, carboxylic acid amide or sulfonic acid as a co-crystal former, and to pharmaceutical compositions comprising said materials. The invention also relates to processes for preparing said crystalline materials and to methods of using said crystalline materials to treat a disease condition in which tyrosine kinase inhibition is beneficial.

21 Claims, 18 Drawing Sheets

MULTICOMPONENT CRYSTALLINE SYSTEM COMPRISING NILOTINIB AND SELECTED CO-CRYSTAL FORMERS

The present invention relates to crystalline materials, preferably comprising or consisting of multicomponent molecular crystals (co-crystals), comprising nilotinib or especially a hydrohalogenide salt of nilotinib, and a carboxylic acid, carboxylic acid ester, carboxylic acid amide, or sulfonic acid as a second component acting as a co-crystal former. The invention further relates to pharmaceutical compositions comprising said materials. The invention also relates to processes for preparing said crystalline materials and multicomponent molecular crystals. The invention also relates to methods of using said crystalline materials or multicomponent molecular crystals to treat a disease condition wherein tyrosine kinase inhibition is beneficial.

Further aspects and advantages of the present invention will become apparent from the ensuing description including the examples and the figures as well as from the enclosed patent claims.

The active substance "hydrohalogenide salt of nilotinib" is the hydrohalogenide salt form of nilotinib, the synonym of 4-methyl-N-[3-(4-methyl-1H-imidazol-1-yl)-5-(trifluoromethyl)phenyl]-3-[(4-pyridin-3-ylpyrimidin-2-yl)amino]benzamide, specifically shown in formula (1):

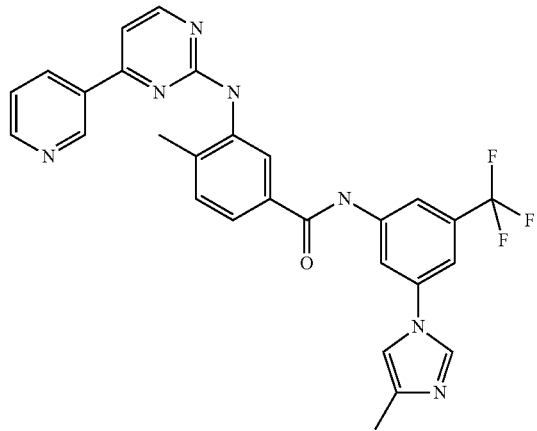

formula (1)

Nilotinib, in the form of the hydrochloride monohydrate salt, is known to act as a tyrosine kinase inhibitor that selectively inhibits the kinases BCR-ABL, KIT, LCK, EPHA3, EPHA8, DDR1, DDR2, PDGFRB, MAPK11 and ZAK. It is useful for the treatment of chronic myelogenous leukemia (CML) and is marketed as Tasigna® (Europe, Australia, Latin America, USA). Nilotinib may have different polymorphic phases.

Nilotinib as a substance and various different polymorphic forms, such as hydrate form A and hydrate form B are already known.

WO 2011/163222 A1 discloses the preparation of nilotinib salts and crystalline forms thereof. The following salts are described: nilotinib HCl, nilotinib fumarate, nilotinib 2-chloromandelate, nilotinib succinate, nilotinib adipate, nilotinib L-tartrate, nilotinib glutarate, nilotinib p-toluenesulfonate, nilotinib camphorsulfonate, nilotinib glutamate, nilotinib palmitate, nilotinib quinate, nilotinib citrate, nilotinib maleate, nilotinib acetate, nilotinib L-malate, nilotinib L-aspartate, nilotinib formate, nilotinib hydrobromide, nilotinib oxalate and nilotinib malonate.

WO 2011/086541 A1 discloses a nilotinib monohydrochloride monohydrate salt and methods for preparing, pharmaceutical compositions comprising, and methods of treatment using said salts.

WO 2010/081443 A2 discloses complexes of some tyrosine kinase inhibitors, or salts thereof, with certain coformers such as alginic acids as well as methods for preparing, pharmaceutical compositions comprising, and methods of treatment using said complexes.

WO 2010/054056 A2 describes several crystalline forms of nilotinib hydrochloride.

WO 2007/015871 A1 discloses the preparation of nilotinib salts and crystalline forms thereof. The salts are mixtures of nilotinib and one acid wherein the acids are selected from the group consisting of hydrochloric acid, phosphoric acid, sulfuric acid, sulfonic acid, methane sulfonic acid, ethane sulfonic acid, benzene sulfonic acid, p-toluene sulfonic acid, citric acid, fumaric acid, gentisic acid, malonic acid, maleic acid, and tartaric acid.

WO 2007/015870 A2 discloses crystalline forms of nilotinib free base and salts thereof as well as the preparation of such salts.

U.S. Pat. No. 7,169,791 B2 discloses several tyrosine kinase inhibitors. Among other compounds, nilotinib is described.

Though there are different polymorphic phases (solid forms) of nilotinib known, there exists a need for (other) crystalline phases of nilotinib for sufficient diversity of crystalline materials to optimize manufacture, improve hygroscopic behavior, dissolution rate, formulation and biological efficiency. The primary objective of the present invention therefore is to develop new crystalline forms of nilotinib showing significantly improved physicochemical properties.

SUMMARY OF THE INVENTION

The invention particularly provides the description of novel crystalline forms of nilotinib, namely crystalline materials comprising nilotinib or especially a hydrohalogenide salt of nilotinib and selected co-crystal formers, and processes for manufacture thereof. The said crystalline forms show improved physical and/or biological characteristics which may assist in the manufacture or formulation of the active compound and to achieve the purity levels and uniformity required for regulatory approval. The said crystalline forms may possess improved pharmacological characteristics, for example, improved bioavailability and/or hygroscopic behavior, thus offering enhanced possibilities to modulate and design improved drug products. Further advantages will become apparent from the following description including several examples.

DETAILED DESCRIPTION OF THE INVENTION

The primary objective of the present invention is achieved by a crystalline material comprising or consisting of
(a) nilotinib, a hydrohalogenide salt of nilotinib, or a mixture of nilotinib and a hydrohalogenide salt of nilotinib, and
(b) a carboxylic acid, carboxylic acid ester, carboxylic acid amide, or sulfonic acid within the same crystalline phase.

Typically, the present invention provides a crystalline material, preferably in the form of multicomponent molecular crystals, comprising or consisting of (a) a hydrohalogenide salt of nilotinib and
(b) a carboxylic acid
within the same crystalline phase.

Optionally, as a further component, (c) water (and/or other) solvents) may be contained.

Crystalline materials according to the invention, wherein (i) the hydrohalogenide salt of nilotinib is a monohydrohalogenide salt of nilotinib, or (ii) the hydrohalogenide salt of nilotinib is a hydrochloride salt of nilotinib, especially a monohydrochloride salt of nilotinib, are particularly preferred.

Component (b) is advantageously a carboxylic acid, preferably a 1,2-dicarboxylic acid or hydroxybenzoic acid, more preferably a 1,2-dicarboxylic acid selected from the group consisting of fumaric acid, maleic acid, and succinic acid, or a hydroxybenzoic acid selected from the group consisting of gentisic acid and gallic acid.

Also preferred are crystalline materials according to the invention, wherein the carboxylic acid is a dicarboxylic acid, especially wherein the dicarboxylic acid is a 1,2-dicarboxylic acid. Further preferred are crystalline materials according to the invention, wherein the carboxylic acid is a hydroxybenzoic acid selected from the group consisting of gentisic acid and gallic acid.

Of specific pharmaceutical interest are cocrystals containing, as component (b), a compound selected from isonicotinamide, gallic acid methyl ester, and naphthalene disulfonic acid.

The novel co-crystalline phases (crystalline materials, preferably in the form of multicomponent molecular crystals) exhibit favorable characteristics regarding hygroscopicity; i.e., they are less prone to water uptake at high relative humidity conditions than the known forms of the monohydrochloride salt. The following table 1 lists the change of the water content for the nilotinib monohydrochloride-fumaric acid co-crystal and nilotinib hydrochloride forms A and B when the relative humidity is changed from 0 to 95% according to the measurement program applied (see FIG. 4).

TABLE 1

Water content change (water uptake) of the of nilotinib monohydrochloride dihydrate form A and nilotinib monohydrochloride monohydrate form B compared to the water content change of the novel co-crystal of nilotinib hydrochloride with fumaric acid.

| Crystalline form | water content change |
|---|---|
| Nilotinib monohydrochloride-fumaric acid co-crystal (prepared as described in example 4; see below) | Δm = 0.4% |
| Nilotinib monohydrochloride dihydrate form A | Δm = 4.2% |
| Nilotinib monohydrochloride monohydrate form B | Δm = 3.2% |

The most important advantage of the co-crystalline systems of this invention (crystalline material, preferably in the form of multicomponent molecular crystals) is the enhanced aqueous solubility, e.g. in comparison to the aqueous solubility of the nilotinib monohydrochloride dihydrate form A and of the nilotinib monohydrochloride monohydrate form B (which are already known from the literature), which has been determined under the same conditions and according to the same protocol as the solubility of the crystalline material according to the invention (as described below).

Determination of the aqueous solubility of the more soluble nilotinib monohydrochloride monohydrate form B resulted in an aqueous solubility of 0.074 milligram per milliliter (0.074 mg/mL) at 25° C. However, even when taking into account the possibility of experimental errors for solubility determinations at the given very low solubility levels, the crystalline materials according to the invention show aqueous solubilities that are at least a factor of 2.2 to 5.7 greater than the solubility of the monohydrochloride monohydrate form B of nilotinib (see table 2). Nilotinib monohydrochloride dihydrate form A is less soluble than the monohydrate form B (see table 2).

TABLE 2

Aqueous solubility of nilotinib monohydrochloride dihydrate form A and nilotinib monohydrochloride monohydrate form B compared to the solubilities of the novel crystalline materials according to the invention (corrected to the effective solubility of the free drug substance); measured after two hours equilibration time.

| Solid-state form/co-crystal | Aqueous Solubility at 25° C. |
|---|---|
| Nilotinib monohydrochloride dihydrate form A | 0.025 mg/mL |
| Nilotinib monohydrochloride monohydrate form B | 0.074 mg/mL |
| Nilotinib monohydrochloride-fumaric acid co-crystal (prepared as described in example 4; see below) | 0.168 mg/mL |
| Nilotinib monohydrochloride- maleic acid co-crystal (prepared as described in example 5; see below) | 0.425 mg/mL |
| Nilotinib monohydrochloride- succinic acid co-crystal (prepared as described in example 7; see below) | 0.161 mg/mL |

As found in own experiments, crystalline materials according to the invention show particularly improved properties if component (b) is a carboxylic acid selected from the group consisting of fumaric acid, maleic acid, succinic acid and gentisic acid (especially the aqueous solubility is improved). It is a very surprising advantageous feature of the fumaric acid co-crystal that both, the solubility and the hygroscopic behavior are substantially improved. Thus particularly preferred are crystalline materials according to the invention, wherein the carboxylic acid is a compound selected from the group consisting of fumaric acid, maleic acid, and succinic acid; or wherein the carboxylic acid is gentisic acid.

The molar ratio of (a) the hydrohalogenide salt of nilotinib and component (b) is preferably in the range from about 2:1 to about 1:2, preferably about 1:1, or about 2:1. The term "about" in this context refers to small deviations in the molar ratio, which may lead to deviations from the given ratio, typically in the range of up to 10%. In particular, the molar ratio is preferably about 1:1 (e.g. ranging from 0.9:1 to 1.1:1) for (a) the hydrohalogenide salt of nilotinib (especially a hydrochloride salt of nilotinib) and (b) fumaric acid, or (a) the hydrohalogenide salt of nilotinib (especially a hydrochloride salt of nilotinib) and (b) succinic acid, and about 2:1 (i.e. from 2.2:1 to 1.8:1) for (a) the hydrohalogenide salt of nilotinib (especially a hydrochloride salt of nilotinib) and (b) maleic acid. Similarly, the composition of the present invention may show a deviation from the 1:1 molar ratio of nilotinib and hydrogen halide (especially hydrogen chloride), which may result in that the hydrohalogenide salt of nilotinib in the product shows a final molar ratio of nilotinib:hydrogen halide (especially hydrogen chloride) in the range from 1.1:1 to 0.9:1, especially from 1.1:1 to 1:1.

Also preferred are crystalline materials according to the invention, wherein the crystalline form is anhydrous or a hydrate (e.g. monohydrate, dihydrate, sesquihydrate, hemihydrate). In particular, crystalline materials comprising (i) (a) a hydrohalogenide salt of nilotinib (especially a hydrochloride salt of nilotinib) and (b) fumaric acid, or (ii) (a) a hydrohalogenide salt of nilotinib (especially a hydrochloride salt of nilotinib) and (b) maleic acid are preferred as an anhydrous form, and a crystalline material comprising (a) a hydrohalogenide salt of nilotinib (especially a hydrochloride salt of nilotinib) and (b) succinic acid is preferred as a hydrate form.

Preferably, the crystalline material comprises or is
A) a multicomponent molecular crystal comprising
  (a) a hydrochloride salt of nilotinib, and
  (b) fumaric acid
  within the same crystalline phase, especially
B) an anhydrous crystalline form as defined under A) consisting essentially of
  (a) a hydrochloride salt of nilotinib, and
  (b) fumaric acid
  having a molar ratio [(a):(b)] in the range from about 1:0.5 to about 1:1.5;
C) a multicomponent molecular crystal comprising
  (a) a hydrochloride salt of nilotinib, and
  (b) maleic acid
  within the same crystalline phase, especially
D) an anhydrous crystalline form as defined under C) consisting essentially of
  (a) a hydrochloride salt of nilotinib, and
  (b) maleic acid
  having a molar ratio [(a):(b)] in the range from about 1:0.4 to about 1:1.5;
E) a multicomponent molecular crystal comprising
  (a) a hydrochloride salt of nilotinib, and
  (b) succinic acid
  within the same crystalline phase, especially
F) a crystalline form as defined under E) consisting essentially of
  (a) a hydrochloride salt of nilotinib,
  (b) succinic acid, and
  (c) water
  having a molar ratio [(a):(b):(c)] of about 1:0.5-1.5:0.5-2;
G) a crystalline form consisting essentially of
  (a) a hydrochloride salt of nilotinib, and
  (b) gentisic acid
  having a molar ratio [(a):(b)] of about 1:0.5-1.5;
H) a crystalline form consisting essentially of
  (a) a hydrochloride salt of nilotinib,
  (b) gentisic acid, and
  (c) water having a molar ratio [(a):(b):(c)] of about 1:0.5-1.5:1-2;
I) a crystalline form consisting essentially of
  (a) a hydrochloride salt of nilotinib, and
  (b) isonicotinamide
  having a molar ratio [(a):(b)] of about 1:0.5-1;
J) a crystalline form consisting essentially of
  (a) a hydrochloride salt of nilotinib, and
  (b) gallic acid methyl ester
  having a molar ratio [(a):(b)] of about 1:0.5-1; and
K) a crystalline form consisting essentially of
  (a) nilotinib and/or a hydrochloride salt of nilotinib,
  (b) naphatalene disulfonic acid, and optionally
  (c) water
  having a molar ratio [(a):(b):(c)] of about 1:0.5-1: 0-1.5.

Especially preferred as hydrochloride salt of nilotinib in the above crystalline forms is the mono-hydrochloride salt.

As already described above, the term "about" in the context of a molar ratio refers to small deviations in the molar ratio, which may lead to deviations from the given ratio, typically in the range of up to 10%.

The term "essentially" in this context means that in addition to the above described components (a), (b) and, if applicable, (c), small amounts of impurities, which cannot be avoided, even after careful purification of the multicomponent molecular crystals, may be present (e.g. preferably in a total amount of below 2 wt. %, more preferably below 1 wt. %, based on the total weight of the multicomponent molecular crystal).

In a preferred embodiment of a crystalline material, (a) a hydrochloride salt of nilotinib and (b) fumaric acid are present in the same crystalline phase, i.e. are forming a co-crystal. Such a crystalline material according to the invention and/or such a multicomponent molecular crystal according to the invention are preferably characterized by exhibiting an X-ray powder diffraction pattern with the following characteristic peaks expressed in d-values (Å) (i.e. showing (at least) the following d-values): 13.6, 7.1, 5.68, 4.84, 4.67, 4.57, 3.87, 3.69, 3.39, 3.36, 3.31, and 3.16, preferably 13.6, 7.1, 7.0, 5.68, 5.61, 4.84, 4.81, 4.67, 4.57, 4.47, 4.32, 4.21, 3.98, 3.87, 3.69, 3.49, 3.39, 3.36, 3.31, 3.28, 3.24, 3.21, 3.16, and 3.09.

The experimental error of the °2θ values as measured by the diffractometer is about ±0.1° to ±0.2°. The experimental error of the d-values depends on the 2θ angle and is approximately ±0.2 for the last given digit, e.g. 7.1±0.2 or 5.68±0.02.

A crystalline material according to the invention and/or the multicomponent molecular crystal according to the invention preferably exhibits a powder X-ray diffraction pattern with characteristic peaks expressed in d-values (Å) as shown in the below table:

| d value [Angstroem] | Intensity |
| --- | --- |
| 13.6 | s |
| 9.2 | w |
| 7.1 | s |
| 7.0 | m |
| 6.8 | w |
| 6.5 | w |
| 5.68 | vs |
| 5.61 | m |
| 4.84 | s |
| 4.81 | s |
| 4.67 | vs |
| 4.57 | s |
| 4.47 | m |
| 4.32 | m |
| 4.26 | w |
| 4.21 | m |
| 4.18 | w |
| 4.09 | w |
| 3.98 | m |
| 3.87 | vs |
| 3.69 | s |
| 3.63 | w |
| 3.57 | w |
| 3.49 | m |
| 3.45 | w |
| 3.39 | vs |
| 3.36 | s |
| 3.31 | s |
| 3.28 | m |
| 3.24 | m |
| 3.21 | m |
| 3.19 | w |
| 3.16 | s |
| 3.09 | m |
| 3.05 | w |

Here and in the following the abbreviations in brackets mean: (vs)=very strong intensity; (s)=strong intensity; (m)=medium intensity; (w)=weak intensity.

A crystalline material according to the invention and/or the multicomponent molecular crystal according to the invention which exhibits a characteristic powder X-ray diffraction pattern substantially as shown in FIG. 1 is particularly preferred.

In an (alternative) preferred embodiment of a crystalline material, (a) a hydrochloride salt of nilotinib and (b) maleic acid are present in the same crystalline phase, i.e. are forming a co-crystal. Such a crystalline material according to the invention and/or such a multicomponent molecular crystal according to the invention are preferably characterized by exhibiting a powder X-ray diffraction pattern with the following characteristic peaks expressed in d-values (Å): 17.2, 15.8, 10.8, 9.1, 7.3, 5.89, 3.66, and 3.60, preferably, 17.2, 15.8, 10.8, 9.1, 8.7, 7.3, 5.89, 5.75, 5.40, 5.22, 3.66, and 3.60.

Especially preferred are a crystalline material according to the invention and/or a multicomponent molecular crystal according to the invention which exhibit a powder X-ray diffraction pattern with characteristic peaks expressed in d-values (Å) as shown in the below table:

| d value [Angstroem] | Intensity |
|---|---|
| 17.2 | m |
| 15.8 | w |
| 10.8 | s |
| 9.1 | m |
| 8.7 | w |
| 7.3 | m |
| 6.9 | w |
| 6.5 | w |
| 6.0 | w |
| 5.89 | s |
| 5.75 | m |
| 5.40 | m |
| 5.22 | m |
| 4.88 | w |
| 4.75 | w |
| 4.41 | w |
| 4.25 | w |
| 4.10 | w |
| 3.93 | m |
| 3.84 | m |
| 3.78 | w |
| 3.66 | vs |
| 3.60 | m |

Here and in the following the abbreviations in brackets mean: (vs)=very strong intensity; (s)=strong intensity; (m)=medium intensity; (w)=weak intensity; (vw)=very weak intensity.

In a further (alternative) preferred embodiment of a crystalline material, (a) a hydrochloride salt of nilotinib and (b) maleic acid are present in the same crystalline phase, i.e. are forming a co-crystal. Such a crystalline material according to the invention and/or such a multicomponent molecular crystal according to the invention are preferably characterized by exhibiting a powder X-ray diffraction pattern with the following characteristic peaks expressed in d-values (Å): 16.6, 15.7, 13.0, 10.7, 9.2, 8.7, 7.3, 6.0, 5.83, 5.39, 5.22, 3.92, 3.65, 3.53, 3.51, 3.44 and 3.40.

Especially preferred are a crystalline material according to the invention and/or a multicomponent molecular crystal according to the invention which exhibit a powder X-ray diffraction pattern with characteristic peaks expressed in d-values (Å) as shown in the below table:

| d value [Angstroem] | Intensity |
|---|---|
| 16.6 | m |
| 15.7 | m |
| 13.0 | m |
| 10.7 | s |
| 9.2 | m |
| 8.7 | s |
| 7.3 | m |
| 6.9 | w |
| 6.5 | w |
| 6.0 | s |
| 5.83 | s |
| 5.70 | w |
| 5.39 | m |
| 5.22 | m |
| 4.99 | w |
| 4.92 | w |
| 4.73 | w |
| 4.62 | w |
| 4.39 | w |
| 4.24 | w |
| 4.10 | w |
| 3.99 | w |
| 3.92 | m |
| 3.78 | w |
| 3.72 | w |
| 3.65 | vs |
| 3.53 | s |
| 3.51 | s |
| 3.44 | Vs |
| 3.40 | M |

A crystalline material according to the invention and/or a multicomponent molecular crystal according to the invention which exhibit a characteristic powder X-ray diffraction patterns substantially as shown in FIG. 2 are particularly preferred.

In an (alternative) preferred embodiment of a crystalline material, (a) a hydrochloride salt of nilotinib and (b) succinic acid are present in the same crystalline phase, i.e. are forming a co-crystal. Such a crystalline material according to the invention and/or such a multicomponent molecular crystal according to the invention are characterized by exhibiting a powder X-ray diffraction pattern with the following characteristic peaks expressed in d-values (Å): 21.1, 3.56, 3.45, and 3.36, preferably 21.1, 10.4, 3.77, 3.68, 3.56, 3.45, and 3.36, or 10.3, 4.58, 3.52 and 3.35.

A preferred crystalline material according to the invention and/or a multicomponent molecular crystal according to the invention preferably exhibit a powder X-ray diffraction pattern with characteristic peaks expressed in d-values (Å) as shown in the below table:

| d value [Angstroem] | Intensity |
|---|---|
| 21.1 | Vs |
| 13.9 | W |
| 10.4 | M |
| 9.2 | W |
| 7.0 | W |
| 6.5 | W |
| 6.1 | Vw |
| 4.61 | W |
| 4.32 | W |
| 3.95 | W |
| 3.77 | M |
| 3.68 | M |
| 3.56 | S |
| 3.45 | S |
| 3.36 | S |

-continued

| d value [Angstroem] | Intensity |
|---|---|
| 3.27 | w |
| 2.99 | w |
| 2.86 | w |

Here and in the following the abbreviations in brackets mean: (vs)=very strong intensity; (s)=strong intensity; (m)=medium intensity; (w)=weak intensity; (vw)=very weak intensity.

A crystalline material according to the invention and/or a multicomponent molecular crystal according to the invention which exhibit a characteristic powder X-ray diffraction pattern substantially as shown in FIG. 3 are particularly preferred.

In a further preferred embodiment of a crystalline material, (a) a hydrochloride salt of nilotinib and (b) gentisic acid are present in the same crystalline phase, i.e. are forming a co-crystal. Such a crystalline material according to the invention and/or such a multicomponent molecular crystal according to the invention are characterized by a powder X-ray diffrac-tion pattern comprising the characteristic peaks expressed in d-values (Å):

A) 16.2, 10.1, 3.45, 3.33, and 3.31, herein designated as nilotinib hydrochloride gentisic acid co-crystal form A; or
B) 16.1, 10.1, 7.3, 6.0, 5.60, 3.58, 3.42, 3.31, 3.28 and 3.25, herein designated as nilotinib hydrochloride gentisic acid co-crystal form B; or
C) 10.1, 7.7, 5.93, 5.02, 3.60, and 3.55, herein designated as nilotinib hydrochlo-ride gentisic acid co-crystal form C; or
D) 16.3, 10.2, 6.1, 5.68, 3.62, 3.58, 3.46, 3.35, 3.32 and 3.29, herein designated as nilotinib hydrochloride gentisic acid co-crystal form D; or
E) 16.2, 15.8, 9.9, 3.41, and 3.29, herein designated as nilotinib hydrochloride gentisic acid co-crystal form E;

especially preferred among the above cocrystals are those exhibiting characteristic peaks (expressed in d-values; Å) at:
16.2, 10.1, 7.4, 6.1, 5.59, 4.61, 3.61, 3.45, 3.33, 3.31 and 3.27, herein designated as nilotinib hydrochloride gentisic acid co-crystal form A; or
16.2, 15.8, 9.9, 7.1, 5.97, 5.53, 4.76, 3.58, 3.53, 3.41, 3.29 and 3.23, herein designated as nilotinib hydrochloride gentisic acid co-crystal form E.

Also preferred is a crystalline material according to the invention, wherein component (b) is a carboxylic acid amide or carboxylic acid ester, especially isonicotinamide or gallic acid methyl ester, and wherein the molar ratio of component (a) to component (b) is from about 2:1 to about 1:1, preferably about 3:2.

An example for this embodiment is a crystalline material according to the invention, wherein component (b) is isonicotinamide, and which is characterized by exhibiting a powder X-ray dif-fraction pattern with the characteristic peaks expressed in d-values (Å): 13.6, 12.4, 6.2, 3.65, 3.54, 3.48 and 3.38, herein designated as the nilotinib hydrochlo-ride isonicotinamide co-crystal.

Another example for this embodiment is a crystalline material according to the invention, wherein component (b) is gallic acid methyl ester, and which is characterized by exhibiting a powder X-ray diffraction pattern with the characteristic peaks expressed in d-values (Å): 17.2, 15.0, 12.3, 11.5, 8.0, 6.8, 5.66, 5.51 and 3.46, herein designated as the nilotinib hydrochloride gallic acid methyl ester co-crystal.

In a further preferred embodiment of a crystalline material, component (a) is nilotinib free base, nilotinib hydrochloride, or a mixture of the free base and the hydrochloride, and component (b) is 1,5-naphtalene disulfonic acid; the cocrystal is characterized by exhibiting a powder X-ray diffraction pattern with the characteristic peaks expressed in d-values (Å):

a) 10.0, 9.4, 9.2, 7.7, 5.95, 4.83, 4.69, 3.53, 3.50, and 3.35, herein designated as nilotinib naphthalene disulfonic acid co-crystal form 1;
b) 18.4, 9.9, 8.3, 7.8, 6.1, 5.86, 4.85, 4.63, 4.42, 4.29, 4.10, 3.87, and 3.68, herein designated as nilotinib naphthalene disulfonic acid co-crystal form 2;
c) 16.6, 5.78, 3.52, 3.46, and 3.40, herein designated as nilotinib naphthalene disulfonic acid co-crystal form 3;
d) 12.0, 7.9, 6.8, 6.6, 5.50, 5.20, 4,74, 4.63, 3.76, 3.68, and 3.48, herein desig-nated as nilotinib naphthalene disulfonic acid co-crystal form 4;
e) 12.0, 7.9, 7.7, 6.8, 6.0, 5.17, 4,72, 4.65, 3.72 and 3.51, herein designated as nilotinib naphthalene disulfonate form 5;
f) 12.0, 6.8, 5.20, 3.76 and 3.69, herein designated as nilotinib naphthalene disulfonate form 6.

A preferred embodiment of the present invention thus preferably comprises a crystalline material essentially consisting of
(a) nilotinib, a hydrohalogenide salt of nilotinib, or a mixture of nilotinib and a hydrohalogenide salt of nilotinib;
(b) fumaric acid, maleic acid, succinic acid, gentisic acid, isonicotinamide, gallic acid methyl ester, or 1,5-naphtalene disulfonic acid, and optionally
(c) up to 2.5 mol of water per mol of nilotinib.

A crystalline material according to the invention and/or the multicomponent molecular crystal according to the invention can be used to treat a disease condition wherein tyrosine kinase inhibition is beneficial.

Therefore, a crystalline material according to the invention and/or the multicomponent molecular crystal according to the invention are preferred for use in the treatment of the human or animal body.

Also preferred are a crystalline material according to the invention and/or the multicomponent molecular crystal according to the invention for use as a medicament (or a part thereof), preferably for the treatment of chronic myelogenous leukemia (CML), more preferably for the treatment of drug-resistant chronic myelogenous leukemia (CML), and/or for tyrosine kinase inhibition.

The present invention further relates to a method of treating a disease, preferably CML, comprising administering (to a person in need thereof) an effective amount of a composition comprising a crystalline material according to the invention and/or a multicomponent molecular crystal according to the invention.

Another aspect of the invention relates to a process for preparing a crystalline material according to the invention and/or a multicomponent molecular crystal according to the invention, comprising the following steps:
(i) producing or providing of nilotinib, a hydrogen halide (preferably hydrogen chloride), and a carboxylic acid, carboxylic acid ester, carboxylic acid amide, or sulfonic acid (preferably fumaric acid, maleic acid, succinic acid, gentisic acid), and
(ii) mixing of all components produced or provided in step (i).

In a preferred process, one, two, or all produced or provided components in step (i) are dissolved in a suitable solvent. Suitable solvents that may be used are typically organic solvents having a water miscibility of at least 10% at room temperature ("polar organic solvents") or mixtures of water with polar organic solvents; especially preferred is methanol. Such solutions are preferably concentrated solutions. The concentration of nilotinib in the resulting mixture of step (ii) preferably ranges from 0.1 to about 300 mg/ml of solvents (including water), more preferably from 10 to 100 mg/ml.

A preferred process according to the invention further comprises step (iii) separating the precipitate and/or evaporation of the solvents (drying).

The process is preferably carried out in the temperature range 20-100° C., preferably 20-80° C. In a preferred process, steps (i) and (ii) are carried out at a temperature in the range from 20-80° C. or the mixture is heated to a temperature from said range, e.g. to about 80° C., to form a solution, especially in case that nilotinib is produced or provided in step (i) as a solid. The solution thus tempered is then preferably cooled before step (iii).

Crystalline materials according to the invention and/or a multicomponent molecular crystal according to the invention as described above or as produced in the process as described above can be used in pharmaceutical compositions in the same way as other forms of nilotinib previously known.

Another object of the invention is a pharmaceutical composition comprising a crystalline material according to the invention and/or a multicomponent molecular crystal according to the invention.

A preferred pharmaceutical composition according to the invention further comprises one, two, three, or more pharmaceutically acceptable carriers, ingredients, or diluents.

The amount of crystalline material according to the invention and/or the multicomponent molecular crystal according to the invention contained in a pharmaceutical composition according to the present invention is not specifically restricted; however, the dose should be sufficient to treat, ameliorate, or reduce the condition.

The amount of the crystalline material according to the invention and/or the multicomponent molecular crystal according to the invention substantially depends on the type of formulation and desired dosages during administration time periods. The amount in an oral formulation may be from 0.1 to 800 mg, preferably from 100 to 600 mg, and more preferably from 300 to 500 mg.

A preferred pharmaceutical composition according to the invention is particularly useful in the treatment of chronic myelogenous leukemia (CML) in connection with need of inhibiting the tyrosine kinase.

Preferred are pharmaceutical compositions according to the invention wherein the carboxylic acid is fumaric acid and which is characterized by at least one characteristic peak in an x-ray powder diffractogram expressed in d-values (Å) selected from 13.6, 7.1, 5.68, 4.84, 4.67, 4.57, 3.87, 3.69, 3.39, 3.36, 3.31, and 3.16; or wherein the carboxylic acid is maleic acid and which is characterized by at least one characteristic peak in an x-ray powder diffractogram expressed in d-values (Å) selected from 17.2, 15.8, 10.8, 9.1, 7.3, 5.89, 3.66, and 3.60; or wherein the carboxylic acid is maleic acid and which is characterized by at least one characteristic peak in an x-ray powder diffractogram expressed in d-values (Å) selected from 16.6, 15.7, 13.0, 10.7, 9.2, 8.7, 7.3, 6.0, 5.83, 5.39, 5.22, 3.92, 3.65, 3.53, 3.51, 3.44 and 3.40; or wherein the carboxylic acid is maleic acid and which is characterized by at least one characteristic peak in an x-ray powder diffractogram expressed in d-values (Å) selected from 10.8, 9.2, 5.4, 5.22, 3.93, 3.66, 3.54, 3.51, and 3.45; or wherein the carboxylic acid is succinic acid and which is characterized by at least one characteristic peak in an x-ray powder diffractogram expressed in d-values (Å) selected from 21.1, 3.56, 3.45, and 3.36, or 10.3, 4.58, 3.52 and 3.35; or wherein the carboxylic acid is gentisic acid and which is characterized by at least one characteristic peak in an x-ray powder diffractogram expressed in d-values (Å) selected from 16.2, 10.1, 3.45, 3.33, and 3.31; or wherein the carboxylic acid is gentisic acid and which is characterized by at least one characteristic peak in an x-ray powder diffractogram expressed in d-values (Å) selected from 16.2, 15.8, 9.9, 3.41, and 3.29.

Pharmaceutical compositions of the present invention can optionally be mixed with other forms of nilotinib and/or other active ingredients. In addition, pharmaceutical compositions of the present invention can contain inactive ingredients such as diluents, carriers, fillers, bulking agents, binders, disintegrants, disintegration inhibitors, absorption accelerators, wetting agents, lubricants, glidants, surface active agents, flavoring agents, and the like.

Oral formulations may be solid formulations such as capsules, tablets, pills and troches, or liquid formulations such as aqueous suspensions, elixirs and syrups. Solid and liquid formulations encompass also incorporation of the present solid form into liquid or solid food.

The crystalline material according to the invention and/or the multicomponent molecular crystal according to the invention may be directly used as powders (micronized particles), granules, suspensions or solutions, or they may be combined together with other pharmaceutically acceptable ingredients in admixing the components and optionally finely divide them, and then filling capsules, composed for example from hard or soft gelatin, compressing tablets, pills or troches, or suspend or dissolve them in carriers for suspensions, elixirs and syrups. Coatings may be applied after compression to form pills.

Suitable pharmaceutically acceptable ingredients are well known for the various types of formulation and may be for example binders (such as natural or synthetic polymers), excipients, lubricants, surfactants, sweetening agents, flavoring agents, coating materials, preservatives, dyes, thickeners, adjuvants, antimicrobial agents and carriers for the various formulation types.

Examples for binders are gum tragacanth, acacia, starch, gelatine, and biological degradable polymers such as homo- or co-polyesters of dicarboxylic acids, alkylene glycols, polyalkylene glycols and/or aliphatic hydroxyl carboxylic acids; homo- or copolyamides of dicarboxylic acids, alkylene diamines, and/or aliphatic amino carboxylic acids; corresponding polyester-polyamide-co-polymers, polyanhydrides, polyorthoesters, polyphosphazene and polycarbonates. The biological degradable polymers may be linear, branched or crosslinked. Specific examples are poly-glycolic acid, poly-lactic acid, and poly-d,l-lactide/glycolide. Other examples for polymers are water-soluble polymers such as polyoxaalkylenes (polyoxaethylene, polyoxapropylene and mixed polymers thereof, poly-acrylamides and hydroxylalkylated polyacrylamides, poly-maleic acid and esters or -amides thereof, poly-acrylic acid and esters or -amides thereof, poly-vinylalcohol und esters or -ethers thereof, poly-vinylimidazole, poly-vinylpyrrolidon, und natural polymers like chitosan, carragenan or hyaluronic aid.

Examples for excipients are phosphates such as dicalcium phosphate.

Examples for lubricants are natural or synthetic oils, fats, waxes, or fatty acid salts like magnesium stearate.

Surfactants may be anionic, cationic, amphoteric or neutral. Examples for surfactants are lecithin, phospholipids, octyl sulfate, decyl sulfate, dodecyl sulfate, tetradecyl sulfate, hexadecyl sulfate and octadecyl sulfate, Na oleate or Na caprate, 1-acylaminoethane-2-sulfonic acids, such as 1-octanoylaminoethane-2-sulfonic acid, 1-decanoylaminoethane-2-sulfonic acid, 1-dodecanoylaminoethane-2-sulfonic acid, 1-tetradecanoylaminoethane-2-sulfonic acid, 1-hexadecanoylaminoethane-2-sulfonic acid, and 1-octadecanoylaminoethane-2-sulfonic acid, and taurocholic acid and taurodeoxycholic acid, bile acids and their salts, such as cholic acid, deoxycholic acid and sodium glycocholates, sodium caprate or sodium laurate, sodium oleate, sodium lauryl sulphate, sodium cetyl sulphate, sulfated castor oil and sodium dioctylsulfosuccinate, cocamidopropylbetaine and laurylbetaine, fatty alcohols, cholesterols, glycerol mono- or -distearate, glycerol mono- or -dioleate and glycerol mono- or -dipalmitate, and polyoxyethylene stearate.

Examples for sweetening agents are sucrose, fructose, lactose or aspartam.

Examples for flavoring agents are peppermint, oil of wintergreen or fruit flavors like cherry or orange flavor.

Examples for coating materials are gelatine, wax, shellac, sugar or biological degradable polymers.

Examples for preservatives are methyl or propylparabens, sorbic acid, chlorobutanol, phenol and thimerosal.

Examples for adjuvants are fragrances.

Examples for thickeners are synthetic polymers, fatty acids and fatty acid salts and esters and fatty alcohols.

Examples for liquid carriers are water, alcohols such as ethanol, glycerol, propylene glycol, liquid polyethylene glycols, triacetin and oils. Examples for solid carriers are talc, clay, microcrystalline cellulose, silica, alumina and the like.

The formulation according to the invention may also contain isotonic agents, such as sugars, buffers or sodium chloride.

Colloidal silicon dioxide may be contained for use as a glidant, carrier, desiccant. Crospovidone may be contained for use as a disintegrant. Hydroxypropyl methylcellulose may be contained for use as a binder. Magnesium stearate may be contained for use as a lubricant. Microcrystalline cellulose may be contained for use as a carrier.

Diluents increase the bulk of a solid pharmaceutical composition and can make a pharmaceutical dosage form containing the composition easier for the patient and care giver to handle. Diluents for solid compositions include, for example, microcrystalline cellulose (e.g., Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., Eudragit®), potassium chloride, powdered cellulose, sodium chloride, sorbitol, or talc.

Carriers for use in the pharmaceutical compositions may include, but are not limited to, lactose, white sugar, sodium chloride, glucose, urea, starch, calcium carbonate, kaolin, crystalline cellulose, or silicic acid.

Binders help bind the active ingredient and other excipients together after compression. Binders for solid pharmaceutical compositions include for example acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel), hydroxypropyl methyl cellulose (e.g. Methocel®), liquid glucose, magnesium aluminum silicate, maltodextrin, methylcellulose, polymethacrylates, povidone (e.g. Kollidon®), Plasdone, pregelatinized starch, sodium alginate, or starch.

Disintegrants can increase dissolution. Disintegrants include, for example, alginic acid, carboxymethylcellulose calcium, carboxymethylcellulose sodium (e.g. Ac-Di-Sol®), Primellose, colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab) and starch.

Disintegration inhibitors may include, but are not limited to, white sugar, stearin, coconut butter, hydrogenated oils, and the like. Absorption accelerators may include, but are not limited to, quaternary ammonium base, sodium laurylsulfate, and the like. Wetting agents may include, but are not limited to, glycerin, starch, and the like. Adsorbing agents may include, but are not limited to, starch, lactose, kaolin, bentonite, colloidal silicic acid, and the like.

A lubricant can be added to the composition to reduce adhesion and ease release of the product from a punch or dye during tableting. Lubricants include for example magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate. Glidants can be added to improve the flowability of non-compacted solid composition and improve the accuracy of dosing.

Excipients that can function as glidants include for example colloidal silicon dioxide, magnesium trisilicate, powdered cellulose, starch, talc and tribasic calcium phosphate. Flavoring agents and flavor enhancers make the dosage form more palatable to the patient. Common flavoring agents and flavor enhancers for pharmaceutical products that can be included in the composition of the present invention include for example maltol, vanillin, ethyl vanillin, menthol, citric acid, fumaric acid, ethyl maltol, and tartaric acid.

Tablets can be further coated with commonly known coating materials such as sugar coated tablets, gelatin film coated tablets, tablets coated with enteric coatings, tablets coated with films, double layered tablets, and multi-layered tablets.

Capsules can be coated with shell made, for example, from gelatin and optionally contain a plasticizer such as glycerin and sorbitol, and an opacifying agent or colorant.

Solid and liquid compositions can also be dyed using any pharmaceutically acceptable colorant to improve their appearance and/or facilitate patient identification of the product and unit dosage level.

In liquid pharmaceutical compositions of the present invention, the crystalline material according to the invention and/or the multicomponent molecular crystal according to the invention are suspended together with any other solid ingredients, which may be dissolved or suspended, in a liquid carrier, such as water, vegetable oil, alcohol, polyethylene glycol, propylene glycol or glycerin.

In suspension the crystalline material according to the invention and/or the multicomponent molecular crystal according to the invention retains its crystalline form. Liquid pharmaceutical compositions can contain emulsifying agents to disperse uniformly throughout the composition an active ingredient or other excipient that is not soluble in the liquid carrier. Emulsifying agents that can be useful in liquid pharmaceutical compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention can also contain viscosity enhancing agents to improve the mouth-feel of the product and/or coat the lining of the gastrointestinal tract. Such agents include for example acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar can be added to improve the taste.

Preservatives and chelating agents such as alcohol, sodium benzoate, butylated hydroxy toluene, butylated hydroxyanisole and ethylenediamine tetraacetic acid can be added at safe levels to improve storage stability.

A liquid pharmaceutical composition according to the present invention can also contain a buffer such as guconic acid, lactic acid, citric acid or acetic acid, sodium guconate, sodium lactate, sodium citrate or sodium acetate.

Selection of excipients and the amounts to use can be readily determined by an experienced formulation scientist in view of standard procedures and reference works known in the art.

A composition for tableting or capsule filing can be prepared by wet granulation. In wet granulation some or all of the active ingredients and excipients in powder form are blended and then further mixed in the presence of a liquid, typically water, which causes the powders to clump up into granules. The granulate is screened and/or milled, dried and then screened and/or milled to the desired particle size. The granulate can then be tableted or other excipients can be added prior to tableting, such as a glidant and/or a lubricant.

A tableting composition can be prepared conventionally by dry blending. For instance, the blended composition of the actives and excipients can be compacted into a slug or a sheet and then comminuted into compacted granules. The compacted granules can be compressed subsequently into a tablet.

As an alternative to dry granulation, a blended composition can be compressed directly into a compacted dosage form using direct compression techniques. Direct compression produces a more uniform tablet without granules.

Excipients that are particularly well-suited to direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, only they are not subjected to a final tableting step.

When shaping the pharmaceutical composition into pill form, any commonly known excipient used in the art can be used. For example, carriers include, but are not limited to, lactose, starch, coconut butter, hardened vegetable oils, kaolin, talc, and the like. Binders used include, but are not limited to, gum arabic powder, tragacanth gum powder, gelatin, ethanol, and the like. Disintegrating agents used include, but are not limited to, agar, laminalia, and the like.

For the purpose of shaping the pharmaceutical composition in the form of suppositories, any commonly known excipient used in the art can be used. For example, excipients include, but are not limited to, polyethylene glycols, coconut butter, higher alcohofs, esters of higher alcohols, gelatin, semisynthesized glycerides, and the like.

When preparing injectable pharmaceutical compositions, solutions and suspensions are sterilized and are preferably made isotonic to blood. Injection preparations may use carriers commonly known in the art. For example, carriers for injectable preparations include, but are not limited to, water, ethyl alcohol, propylene glycol, ethoxylated isostearyl alcohol, polyoxylated isostearyl alcohol, and fatty acid esters of polyoxyethylene sorbitan. One of ordinary skill in the art can easily determine with little or no experimentation the amount of sodium chloride, glucose, or glycerin necessary to make the injectable preparation isotonic.

Additional ingredients, such as dissolving agents, buffer agents, and analgesic agents may be added. If necessary, coloring agents, preservatives, perfumes, seasoning agents, sweetening agents, and other medicines may also be added to the desired preparations during the treatment.

The crystalline material, the multicomponent molecular crystal or, respectively, the pharmaceutical composition according to the invention may also be formulated as effervescent tablet or powder, which disintegrate in an aqueous environment to provide a drinking solution.

A syrup or elixir may additionally contain sucrose or fructose as sweetening agent, a preservative like methylparaben, a dye and/or a flavouring agent.

The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages may be conveniently presented in unit dosage form and prepared by any of the methods well known in the art of pharmacy.

Dosage forms include solid dosage forms, like tablets, powders, capsules, suppositories, sachets, troches and losenges as well as liquid suspensions and elixirs. While the description is not intended to be limiting, the invention is also not intended to pertain to true solutions of nilotinib whereupon the properties that distinguish crystalline material according to the invention and/or the multicomponent molecular crystal according to the invention are lost. However, the use of the novel forms to prepare such solutions is considered to be within the contemplation of the invention.

Capsule dosages, of course, will contain the solid composition within a capsule which may be made of gelatin or other conventional encapsulating material. Tablets and powders may be coated. Tablets and powders may be coated with an enteric coating. The enteric coated powder forms may have coatings comprising phthalic acid cellulose acetate, hydroxypropylmethyl cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric coating.

Slow release formulations may also be prepared from the crystalline material according to the invention and/or the multicomponent molecular crystal according to the invention in order to achieve a controlled release of the active agent in contact with the body fluids in the gastro intestinal tract, and to provide a substantial constant and effective level of the active agent in the blood plasma. The crystal forms may be embedded for this purpose in a polymer matrix of a biological degradable polymer, a water-soluble polymer or a mixture of both, and optionally suitable surfactants. Embedding can mean in this context the incorporation of microparticles in a matrix of polymers. Controlled release formulations are also obtained through encapsulation of dispersed microparticles or emulsified micro-droplets via known dispersion or emulsion coating technologies.

The crystalline material according to the invention and/or the multicomponent molecular crystal according to the invention are also useful for administering a combination of therapeutic effective agents to an animal. Such a combination therapy can be carried out in using at least one further therapeutic agent which can be additionally dispersed or dissolved in a formulation.

The crystalline material according to the invention and/or the multicomponent molecular crystal according to the invention and formulations containing the same can be administered in combination with other therapeutic agents that are effective to treat a given condition to provide a combination therapy.

The crystalline material according to the invention and/or the multicomponent molecular crystal according to the invention are highly suitable for effective treatment of disorders in connection with the need of inhibiting the BCR-ABL, KIT, LCK, EPHA3, EPHA8, DDR1, DDR2, PDGFRB, MAPK11, and/or ZAK tyrosine kinases, in particular in the treatment of chronic myelogenous leukemia.

The following examples illustrate the invention. Wherever noted, room temperature (r.t.) depicts a temperature from the range 22±3° C.; percentages are given by weight, if not indicated otherwise.

Abbreviations:

DVS differential vapor sorption

HPLC high pressure liquid chromatography

NMR nuclear magnetic resonance

FTIR Fourier-transformation infrared spectrometry

PXRD powder x-ray diffraction

XRPD x-ray powder diffractogram

TG-FTIR Thermogravimetry coupled with Fourier Transform Infrared Spectroscopy

Instrumental Parameters and Measurement Procedures

Powder X-ray diffraction (PXRD): Stoe Stadi P; Mythen1 K Detector; $CU_{K-alpha}$ radiation; standard measurement conditions: transmission; 40 kV and 40 mA tube power; curved Ge monochromator; 0.02°2θ step size, 12 s step time, 1.5-50.5°2θ scanning range; detector mode: step scan; 1 °2θ detector step; standard sample preparation: 10 to 20 mg sample was placed between two acetate foils; sample holder: Stoe transmission sample holder; the sample was rotated during the measurement.

Thermogravimetry coupled with Fourier Transform Infrared Spectroscopy (TG-FTIR): TG-FTIR was performed on a Netzsch Thermo-Microbalance TG 209, which is coupled to a Bruker FT-IR Spectrometer Vector 22. The measurements were carried out with aluminum crucibles with a micro pinhole under a nitrogen atmosphere and at a heating rate of 10° C./min over the range 25-250° C.

HPLC: HPLC was carried out on a TSP HPLC chromatograph (UV3000, AS3000, P4000, SCM1000 software version 4.1). The column type used was a Waters XTerra MS C18, 100×4.6 mm, 5 μm (CC01C). Mobile phase A was $H_2O$/ACN 95:5+0.1% TFA and mobile phase B was $H_2O$/ACN 5:95+0.1% TFA. The applied flow rate was 1.0 mL per minute, the injection volume was 10 microliter and the detection wavelength was 240 nm. The gradient was at 0 min 100% mobile phase A, at 20 min 100% mobile phase B, from 20 to 30 minutes pure mobile phase A.

NMR: The H-NMR spectra were recorded using a Bruker DPX300 instrument. Generally, D6-DMSO was used as the solvent.

EXAMPLES

Example 1

Nilotinib Hydrochloride-fumaric Acid Co-crystal

Figure 1:
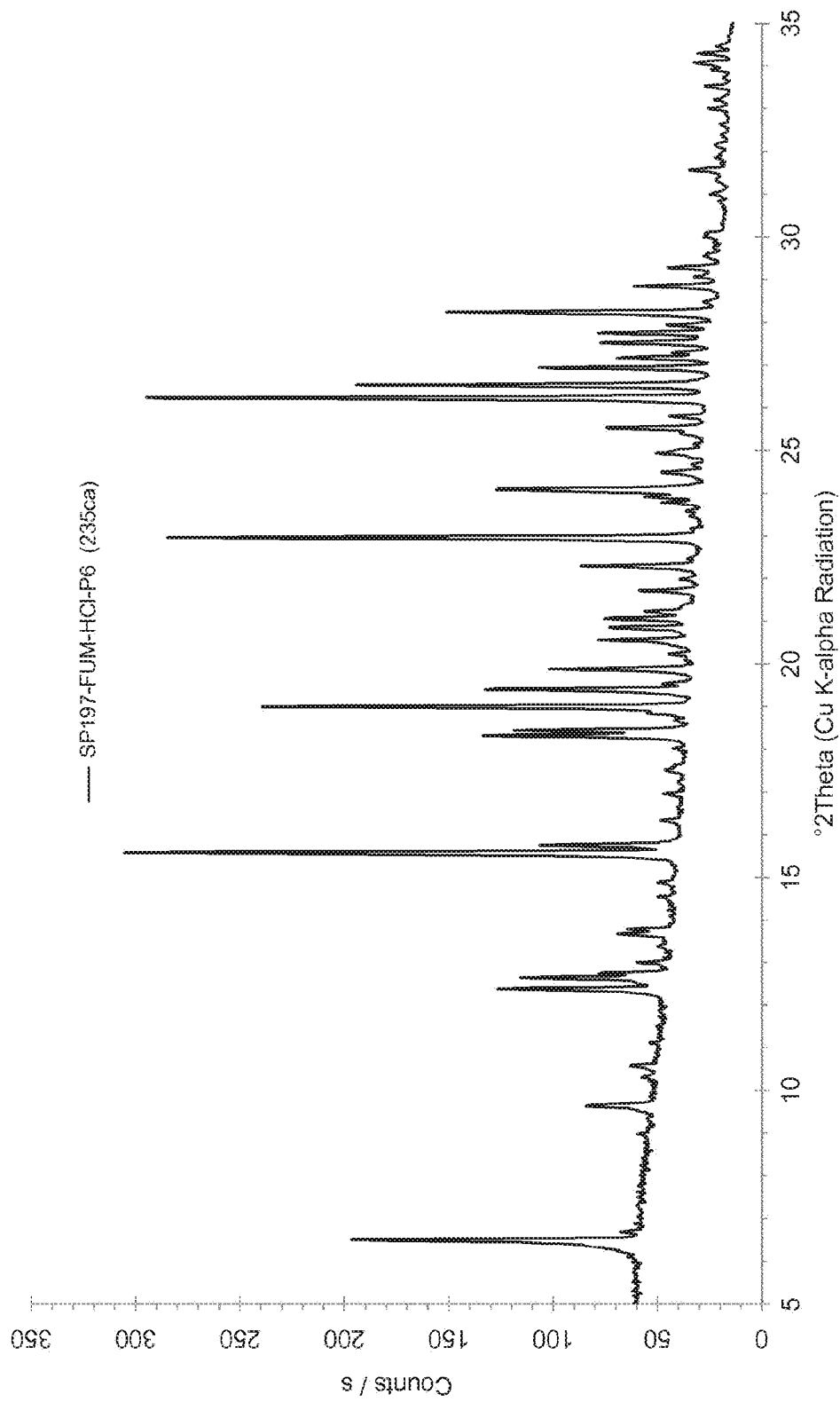
FIG. 1: Powder X-ray diffraction pattern of a nilotinib hydrochloride-fumaric acid co-crystal.

To 100 mg of nilotinib free base form A and 22 mg of fumaric acid 10 mL methanol and 29 μL of hydrochloric acid (c=6 M) is added and the mixture is stirred at 50° C. for 15 min. The resulting solution is filtered (0.2 μm PTFE filter) and evaporated under nitrogen flow at r.t. To the solid residue 2 mL of TBME is added and the suspension is stirred at r.t. for 4 days. The obtained solid is collected by filtration and characterized by PXRD. The PXRD pattern essentially corresponds to the pattern as shown in FIG. 1.

Example 2

Nilotinib Hydrochloride-fumaric Acid Co-crystal

To 107 mg of nilotinib free base and 24 mg of fumaric acid 5 mL of methanol and 31.5 μL of hydrochloric acid (c=6 M) is added. The mixture is dissolved upon heating. The solution is evaporated under nitrogen flow at r.t. To the obtained solid 2 mL of TBME is added, seeded with solid from example 1 and the obtained suspension is stirred at r.t. overnight. The yellow solid is collected by filtration and characterized by PXRD, HNMR, TG-FTIR and chloride determination.

Example 3

Nilotinib Hydrochloride-fumaric Acid Co-crystal

To 202 mg of nilotinib free base form A and 44 mg of fumaric acid 2 mL of methanol and 63 μL of hydrochloric acid (c=6 M) is added. The mixture is seeded with solid from example 2. The solution is evaporated under nitrogen flow at r.t. 2 mL of 2-propanol is added and stirred at r.t. overnight. The obtained solid is collected by filtration and characterized by PXRD, HNMR and chloride determination. TG-FTIR shows that the obtained material is neither a solvate, nor a hydrate. NMR spectroscopy confirms a molar ratio of nilotinib to fumaric acid of about 1:1 and the chloride content was found to be 5.4% which is essentially consistent with a co-crystal of the monohydrochloride salt.

The results of the PXRD determination are shown in Table 3. The resulting spectrum is shown in FIG. 1. The experimental error of the °2θ values is about ±0.1°.

TABLE 3

Powder X-ray diffraction peaks for nilotinib hydrochloride-fumaric acid co-crystal. The experimental error of the °2θ values is about ±0.1°.

| Pos. [°2θ.] | d-spacing [Å] | Qualitative Intentsity |
|---|---|---|
| 6.5 | 13.6 | s |
| 9.6 | 9.2 | w |
| 12.4 | 7.1 | s |
| 12.6 | 7.0 | m |
| 13.0 | 6.8 | w |
| 13.7 | 6.5 | w |
| 15.6 | 5.68 | vs |
| 15.8 | 5.61 | m |
| 18.3 | 4.84 | s |
| 18.4 | 4.81 | s |
| 19.0 | 4.67 | vs |
| 19.4 | 4.57 | s |
| 19.9 | 4.47 | m |
| 20.6 | 4.32 | m |
| 20.8 | 4.26 | w |
| 21.1 | 4.21 | m |
| 21.3 | 4.18 | w |
| 21.7 | 4.09 | w |
| 22.3 | 3.98 | m |
| 23.0 | 3.87 | vs |
| 24.1 | 3.69 | s |
| 24.5 | 3.63 | w |
| 25.0 | 3.57 | w |
| 25.5 | 3.49 | m |
| 25.8 | 3.45 | w |
| 26.2 | 3.39 | vs |
| 26.5 | 3.36 | s |
| 26.9 | 3.31 | s |
| 27.2 | 3.28 | m |
| 27.5 | 3.24 | m |
| 27.8 | 3.21 | m |
| 27.9 | 3.19 | w |
| 28.2 | 3.16 | s |
| 28.8 | 3.09 | m |
| 29.3 | 3.05 | w |

Example 4

Nilotinib Hydrochloride-fumaric Acid Co-crystal

To about 531 mg of nilotinib free base 10 mL of methanol is added and about 117 mg of fumaric acid and 167 μL of hydrochloric acid (c=6 M) is added. At 65° C. a clear solution is obtained. During cooling overnight a nitrogen flow of 20 mL/min is applied. A thick suspension is obtained at r.t. and nitrogen flow is increased to about 80 mL/min until about 7 mL of solvent remain. The suspension is stirred for about 3 hours at 40° C. About 3 mL of 2-propanol are added and then the suspension is stirred at r.t. overnight. At 40° C. the suspension is easy to stir. The solvent is evaporated with nitrogen flow for about 6 hours, then stirred at r.t. About 3 mL of solvent are evaporated under nitrogen flow. The yellow solid is collected by filtration and characterized by PXRD, DVS, elemental composition analysis, and aqueous solubility determination. Powder X-ray diffraction reveals a PXRD pattern essentially as shown in FIG. 1 and the elemental composition analysis shows the following contents: carbon 56.3%, hydrogen 4.1%, nitrogen 14.9%, fluorine 8.3%, oxygen 12.2%, chloride 4.9%. This composition is consistent with a crystalline single phase composition containing nilotinib hydrochloride and fumaric acid with a molar ratio of 1:1. Dynamic vapor sorption shows that the co-crystal shows highly desirable properties as the highest water up-take at 95% relative humidity is only about 0.4%.

Example 5

Nilotinib Hydrochloride-maleic Acid Co-crystal

To 99 mg of nilotinib free base and 22 mg of maleic acid 4 mL methanol and 32 μL of hydrochloric acid (c=6 M) is added. The solid is dissolved upon heating. The resulting solution is evaporated under nitrogen flow at r.t. until a dry solid residue is obtained. To the solid 2 mL of 2-propanol is added and the suspension is stirred at r.t. for 3 days. The solid is collected by filtration and characterized by PXRD, HNMR and chloride determination. TG-FTIR shows a mass loss of about 0.5% upon heating to 150° C. at a rate of 10° C. per minute, suggesting that the obtained material is neither a solvate, nor a hydrate. The HNMR spectrum is consistent with a molar ratio of nilotinib free base to maleic acid of 2:1 and the chloride determination reveals a chloride content of 4.7% which is essentially consistent with a 1:1 molar ratio of nilotinib to hydrochloric acid.

Figure 2:
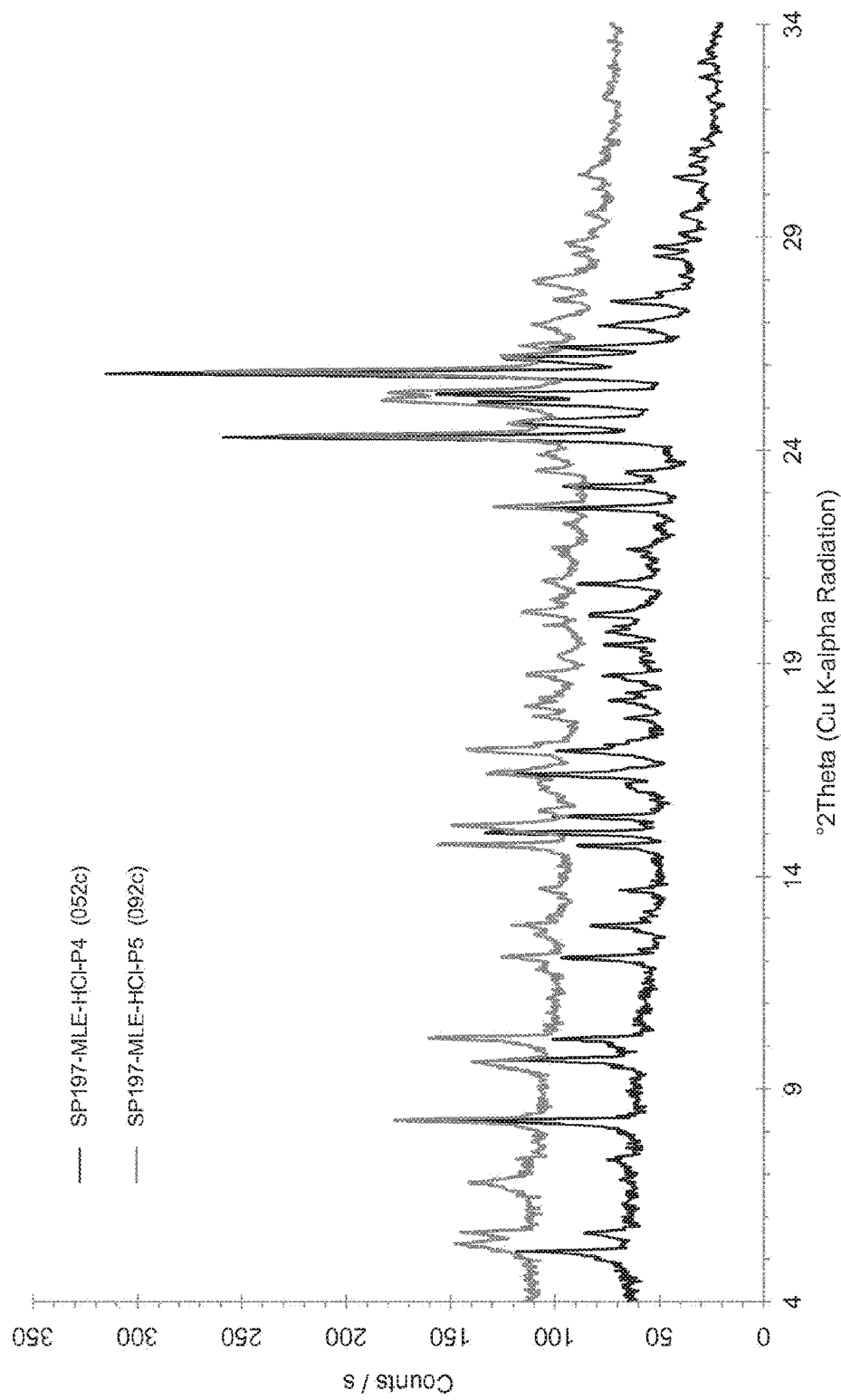
FIG. 2: Powder X-ray diffraction patterns of a nilotinib hydrochloride-maleic acid co-crystals.

The results of the PXRD determination are shown in Table 4. The resulting PXRD pattern is shown in FIG. 2 (lower trace). The experimental error of the °2θ values is about ±0.1°.

TABLE 4

Powder X-ray diffraction peaks for nilotinib hydrochloride-maleic acid co-crystal. The experimental error of the °2θ values is about ±0.1°.

| Pos. [°2θ.] | d-spacing [Å] | Qualitative Intentsity |
|---|---|---|
| 5.1 | 17.2 | m |
| 5.6 | 15.8 | w |
| 8.2 | 10.8 | s |
| 9.7 | 9.1 | m |
| 10.1 | 8.7 | w |
| 12.1 | 7.3 | m |
| 12.8 | 6.9 | w |
| 13.7 | 6.5 | w |
| 14.7 | 6.0 | w |
| 15.0 | 5.89 | s |
| 15.4 | 5.75 | m |
| 16.4 | 5.40 | m |
| 17.0 | 5.22 | m |
| 18.2 | 4.88 | w |
| 18.7 | 4.75 | w |
| 20.1 | 4.41 | w |
| 20.9 | 4.25 | w |
| 21.7 | 4.10 | w |
| 22.6 | 3.93 | m |
| 23.1 | 3.84 | m |
| 23.5 | 3.78 | w |
| 24.3 | 3.66 | vs |
| 24.7 | 3.60 | m |
| 25.1 | 3.54 | s |
| 25.3 | 3.51 | s |
| 25.8 | 3.45 | vs |
| 26.2 | 3.40 | m |
| 26.4 | 3.37 | m |

Example 6

Nilotinib Hydrochloride-maleic Acid Co-crystal

To 203 mg of nilotinib free base and 45 mg of maleic acid 2 mL of methanol and 63 μL of hydrochloric acid (c=6 M) is added. The mixture is seeded with solid from example 5 and the solvent is evaporated under nitrogen flow. To the solid 3 mL of 2-propanol is added and stirred at r.t. overnight. The solid is collected by filtration and characterized by PXRD, HNMR, TG-FTIR and chloride determination. TG-FTIR shows a mass loss of about 2% upon heating to 150° C. at a rate of 10° C. per minute, suggesting that the obtained material contains some residual water and isopropanol. The HNMR spectrum is consistent with a molar ratio of nilotinib free base to maleic acid of 2:1 and the chloride determination reveals a chloride content of 5.6% which is essentially consistent with a 1:1 molar ratio of nilotinib to hydrochloric acid. The results of the PXRD determination are shown in Table 5. The experimental error of the °2θ values is about ±0.1°. The resulting PXRD pattern is shown in FIG. 2 (upper trace).

TABLE 5

Powder X-ray diffraction peaks for nilotinib hydrochloride-maleic acid co-crystal. The experimental error of the °2θ values is about ±0.1°.

| Pos. [°2θ.] | d-spacing [Å] | Qualitative Intentsity |
|---|---|---|
| 5.3 | 16.6 | m |
| 5.6 | 15.7 | m |
| 6.8 | 13.0 | m |
| 8.2 | 10.7 | s |
| 9.6 | 9.2 | m |
| 10.2 | 8.7 | s |
| 12.1 | 7.3 | m |
| 12.8 | 6.9 | w |
| 13.7 | 6.5 | w |
| 14.7 | 6.0 | s |
| 15.2 | 5.83 | s |
| 15.5 | 5.70 | w |
| 16.4 | 5.39 | m |
| 17.0 | 5.22 | m |
| 17.8 | 4.99 | w |
| 18.0 | 4.92 | w |
| 18.7 | 4.73 | w |
| 19.2 | 4.62 | w |
| 20.2 | 4.39 | w |
| 20.9 | 4.24 | w |
| 21.7 | 4.10 | w |
| 22.3 | 3.99 | w |
| 22.7 | 3.92 | m |
| 23.5 | 3.78 | w |
| 23.9 | 3.72 | w |
| 24.4 | 3.65 | vs |
| 24.7 | 3.61 | w |
| 25.2 | 3.53 | s |
| 25.4 | 3.51 | s |
| 25.8 | 3.44 | vs |
| 26.2 | 3.40 | m |
| 26.5 | 3.37 | w |
| 27.0 | 3.30 | w |
| 27.5 | 3.24 | w |

Example 7

Nilotinib Hydrochloride-succinic Acid Co-crystal

To 100 mg of nilotinib free base and 23 mg of succinic acid 4 mL of methanol and 32 μL of hydrochloric acid (c=6 M) is added. The mixture is dissolved upon heating and the solution is evaporated under nitrogen flow at r.t. To the solid 2 mL of 2-propanol is added and stirred at r.t. for 3 days. The solid is collected by filtration and characterized by PXRD, HNMR, TG-FTIR, and chloride determination and aqueous solubility determination. TG-FTIR shows a mass loss of about 5% upon heating to 150° C. at a rate of 10° C. per minute which is attributable to loss of water. The HNMR spectrum is consistent with a molar ratio of nilotinib free base to succinic acid of 1:1 and the chloride determination reveals a chloride content of 4.8% which is essentially consistent with a 1:1 molar ratio of nilotinib to hydrochloric acid.

The results of the PXRD determination are shown in Table 6. The resulting PXRD pattern is shown in the lower trace of FIG. 3. The experimental error of the °2θ values is about ±0.1°.

TABLE 6

Powder X-ray diffraction peaks for nilotinib hydrochloride-succinic acid co-crystal.

| Pos. [°2θ.] | d-spacing [Å] | Qualitative Intentsity |
|---|---|---|
| 4.3 | 21.1 | vs |
| 6.3 | 13.9 | w |
| 8.5 | 10.4 | m |
| 9.6 | 9.2 | w |
| 12.7 | 7.0 | w |
| 13.6 | 6.5 | w |
| 14.5 | 6.1 | vw |
| 19.2 | 4.61 | w |
| 20.6 | 4.32 | w |
| 22.5 | 3.95 | w |
| 23.6 | 3.77 | m |
| 24.2 | 3.68 | m |
| 25.0 | 3.56 | s |
| 25.8 | 3.45 | s |
| 26.5 | 3.36 | s |
| 27.3 | 3.27 | w |
| 29.9 | 2.99 | w |
| 31.2 | 2.86 | w |

Example 8

Nilotinib Hydrochloride-succinic Acid Co-crystal

Figure 3:
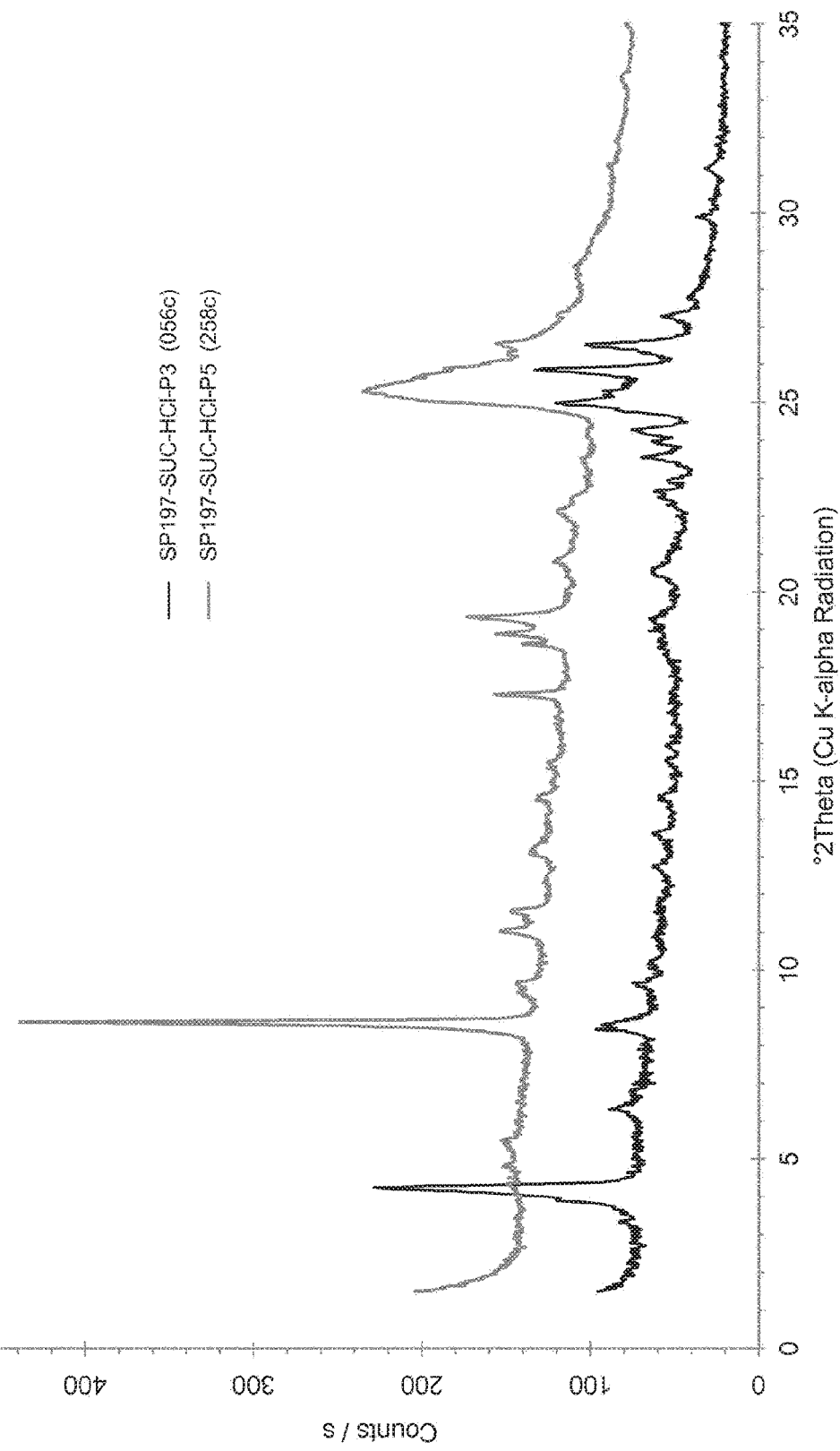
FIG. 3: Powder X-ray diffraction patterns of a nilotinib hydrochloride-succinic acid co-crystals.

To 1042 mg of nilotinib free base and 225 mg of succinic acid 7 mL of methanol and 320 μL of hydrochloric acid (c=6 M) and a few mg of the nilotinib hydrochloride succinic acid co-crystal according to example 7 is added. The mixture is stirred at room temperature for one day the six mL water is added to the mixture and stirring is continued at r.t. after one day of stirring the solvents are evaporated under nitrogen at r.t. and 7 mL isopropanol is added to the dry residue. Then more seed crystals are added and the mixture is stirred at room temperature for another day before the solid is separated by filtration. The product is dried under vacuum at r.t. and investigated by PXRD, and elemental composition analysis. Powder X-ray diffraction reveals a PXRD pattern as shown in FIG. 3 (upper trace) and the elemental composition analysis reveals the following contents: carbon 55.6%, hydrogen 4.5%, nitrogen 15.8%, fluorine 9.1%, oxygen 9.2%, chloride 5.6%. This composition is consistent with a crystalline single phase composition containing nilotinib hydrochloride and succinic acid and water with a molar ratio of 2:1:2.

Example 9

Figure 4:
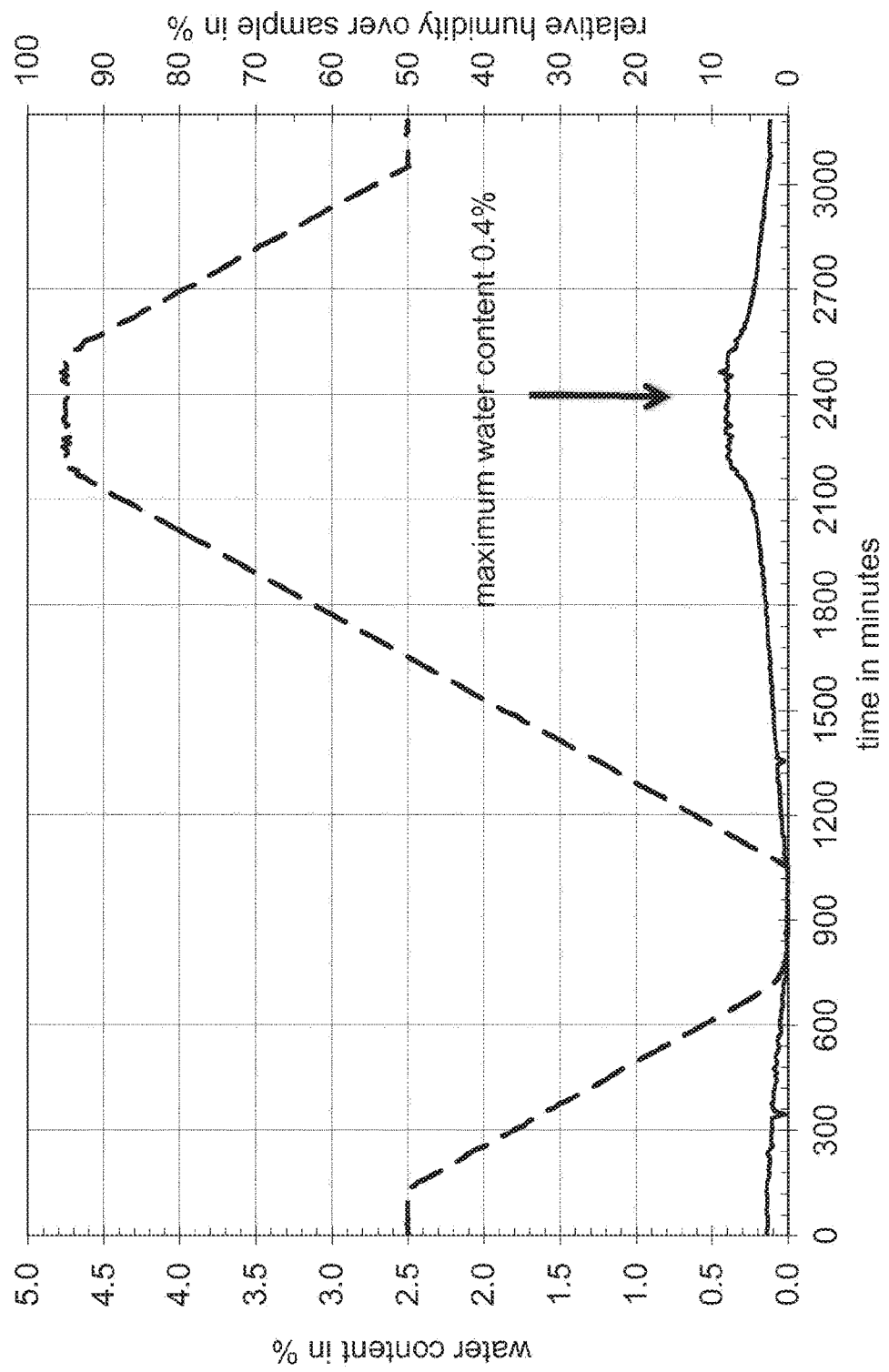
FIG. 4: DVS result for a nilotinib hydrochloride-fumaric acid co-crystal. The dashed line reflects the applied measurement program (right y-axis) and the solid line shows the water content of the sample at a given relative humidity (left y-axis).

Water content of the material obtained in examples 1-8 and 11 and 16 is determined by TG-FTIR and differential vapour sorption. Results are reported in the preparation examples, in Table 1 and in FIG. 4.

Example 10

Solubility experiments using the crystalline material obtained in examples 1-8 and 11 and 16 are carried out following the method described in WO 2012/143308 page 12. Results are reported in Table 2 further above.

Example 11

Preparation of the Nilotinib Hydrochloride-gentisic Acid Co-crystal Form A

Figure 5:
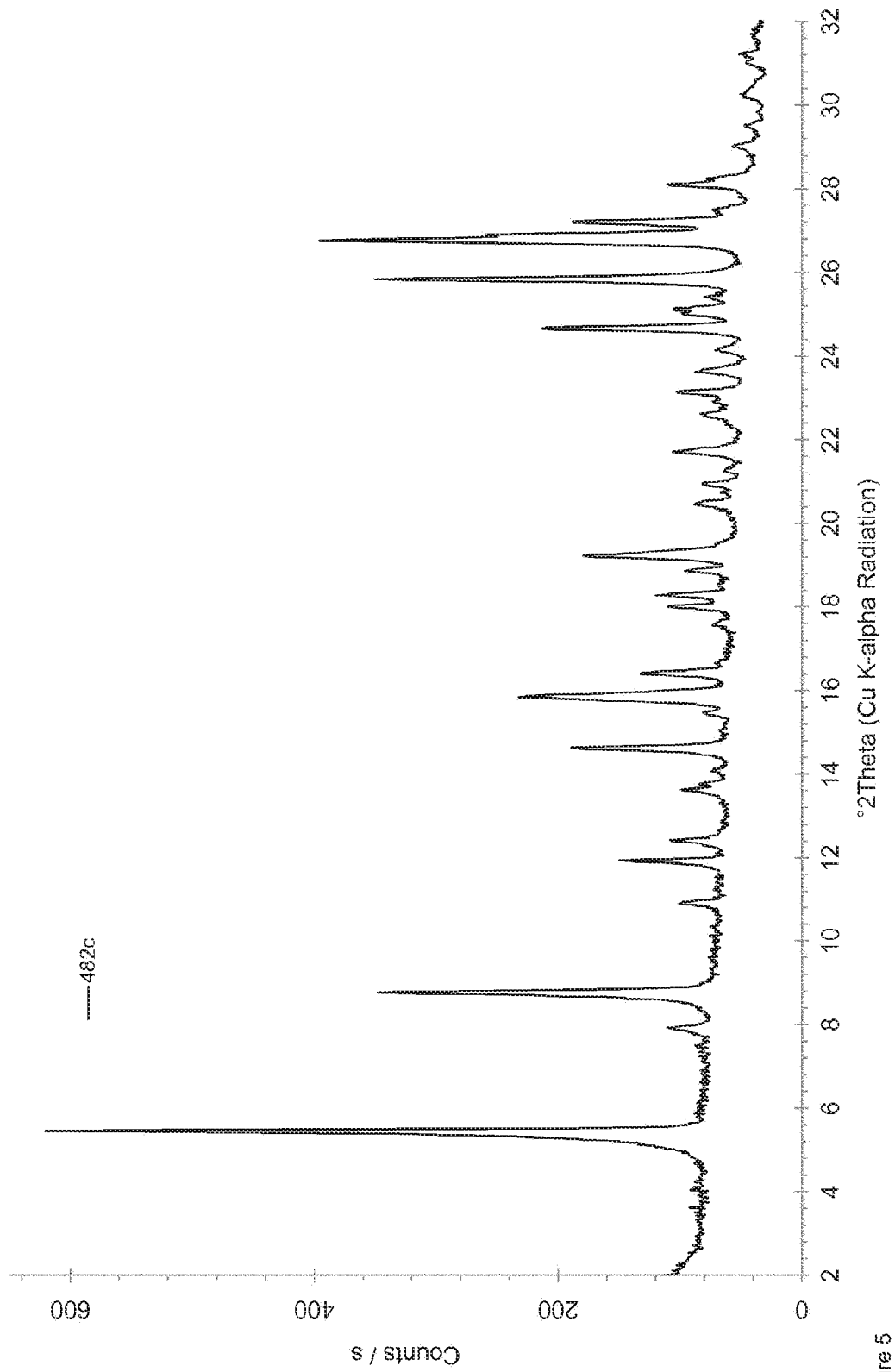
FIG. 5: Powder X-ray diffraction pattern of a nilotinib hydrochloride-gentisic acid co-crystal form A.

To 265 mg nilotinib free base (~0.5 mmol) is added 12.0 ml of a 0.05 M stock solution of gentisic acid (Fluka #37550) in methanol and 260 microliter 2 M hydrochloric acid. Dissolution of the solid is achieved by heating to reflux temperature, thereafter let the solution cool to 40° C. and the solvent evaporate under a steady flow of nitrogen (about 20 ml/minute). To the obtained dry residue is added 5.0 ml heptane and the mixture is stirred at 40° C. for about one hour, then let cool to room temperature and stir for another hour before the solid product is separated by filtration and powder X-ray diffraction is performed. The crystalline solid is dried under vacuum at 50° C. for about 18 hours. The obtained PXRD pattern, as shown in FIG. 5, shows peaks at positions as indicated in Table 11. The analysis by H-NMR reveals a ratio of nilotinib to gentisic acid of 1:1. Further analysis by elemental composition analysis indicates 56.5% carbon, 4.4% hydrogen, 12.4% nitrogen, 13.7% oxygen, 7.5% fluorine, and 5.0% chloride. This composition is consistent with a multicomponent crystal of the formula $C_{28}H_{22}F_3N_7O \cdot HCl \cdot C_7H_6O_4 \cdot H_2O$ and a molecular weight of 738.1 g/mol.

Example 12

Preparation of the Nilotinib Hydrochloride-gentisic Acid Co-crystal Form B

Figure 6:
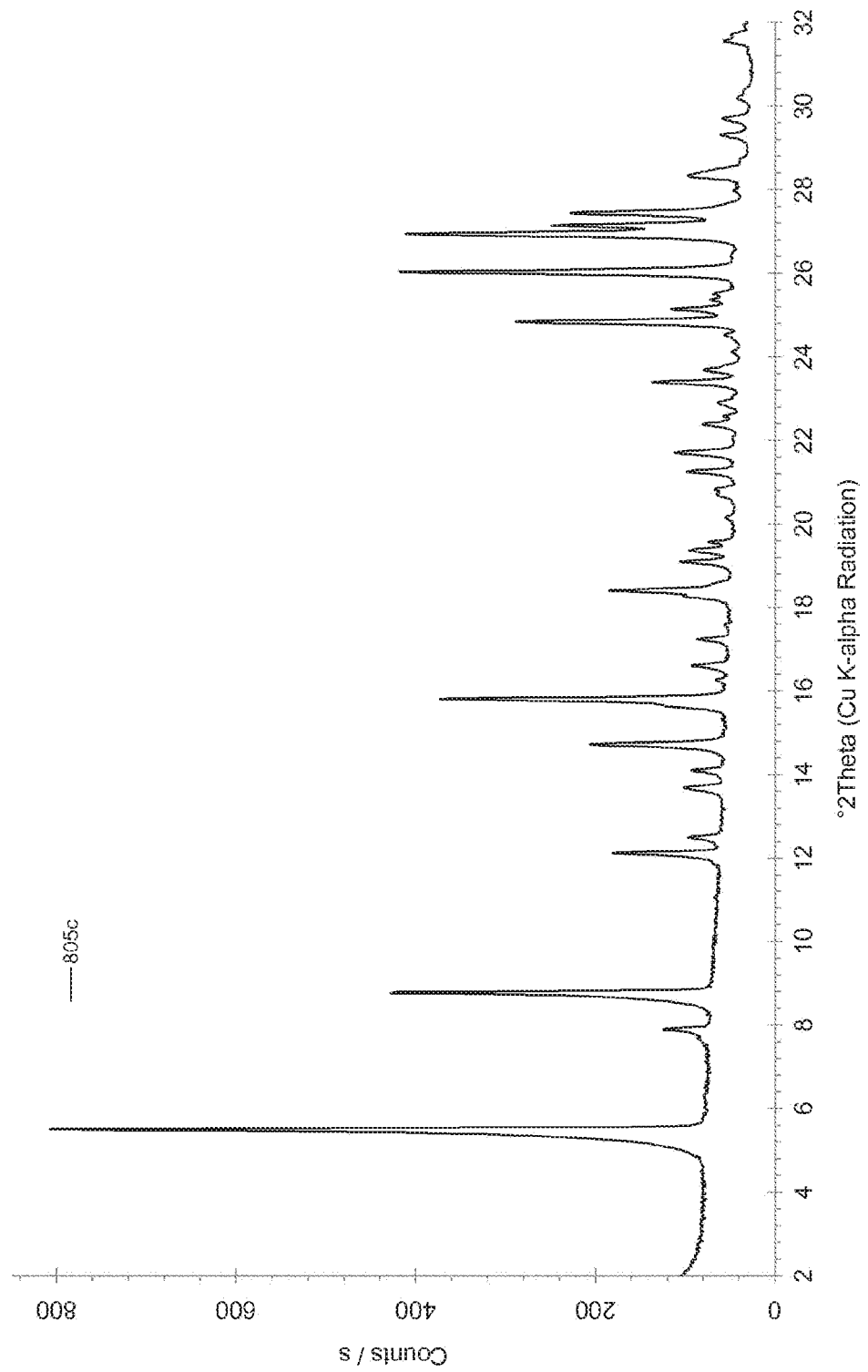
FIG. 6: Powder X-ray diffraction pattern of a nilotinib hydrochloride-gentisic acid co-crystal form B.

To 530 mg nilotinib free base (~1.0 mmol) is added 10.0 ml ethanol, 525 microliter of 2 M hydrochloric acid. Dissolution of the solid is achieved by heating to reflux temperature, thereafter let the solution cool to 50° C. and 330 mg gentisic acid (Fluka #37550) is added to the solution. A suspension is obtained which is stirred at 50° C. overnight. After overnight stirring the suspension temperature is changed from 50° C. to 30° C. and back to 50° C. three times (cycling) over about six hours while about 40-50% of the ethanol is removed under a slight flow of nitrogen. The suspension is filtered and powder X-ray diffraction is performed. The crystalline solid is dried under vacuum at 50° C. for about 18 hours. The obtained PXRD pattern, as shown in FIG. 6, is designated as nilotinib hydrochloride-gentisic acid co-crystal form B. The analysis by H-NMR reveals a ratio of nilotinib to gentisic acid of 1:1.

Example 13

Preparation of the Nilotinib Hydrochloride-gentisic Acid Co-crystal Form A 3.0 ml Heptane is added to 200 mg nilotinib hydrochloride-gentisic acid co-crystal form B according to example 12 and the obtained suspension is stirred at 40° C. for about 20 hours. Then the solid is filtered off and PXRD is performed. The product shows essentially the PXRD pattern of nilotinib hydrochloride-gentisic acid co-crystal form A as depicted in FIG. 5.

Example 14

Preparation of the Nilotinib Hydrochloride-gentisic Acid Co-crystal Form B

To 530 mg nilotinib free base (~1.0 mmol) is added 10.0 ml methanol, the suspension is sonicated and heated to 65° C., and 0.5 ml of 2M aqueous hydrochloric acid and 161 mg gentisic acid (Fluka #37550) is added. After about 15 minutes a clear solution is obtained. Then let the solution cool to room temperature and carryout seeding with few mg of nilotinib hydrochloride-gentisic acid co-crystal form A as the seed crystals. A suspension forms which is stirred at room temperature overnight. Then the solid product is filtered off and powder X-ray diffraction is performed. The obtained PXRD pattern of the nilotinib hydrochloride-gentisic acid co-crystal form B is shown in FIG. 6 and the peak locations are presented in Table 12.

Example 15

Figure 7:
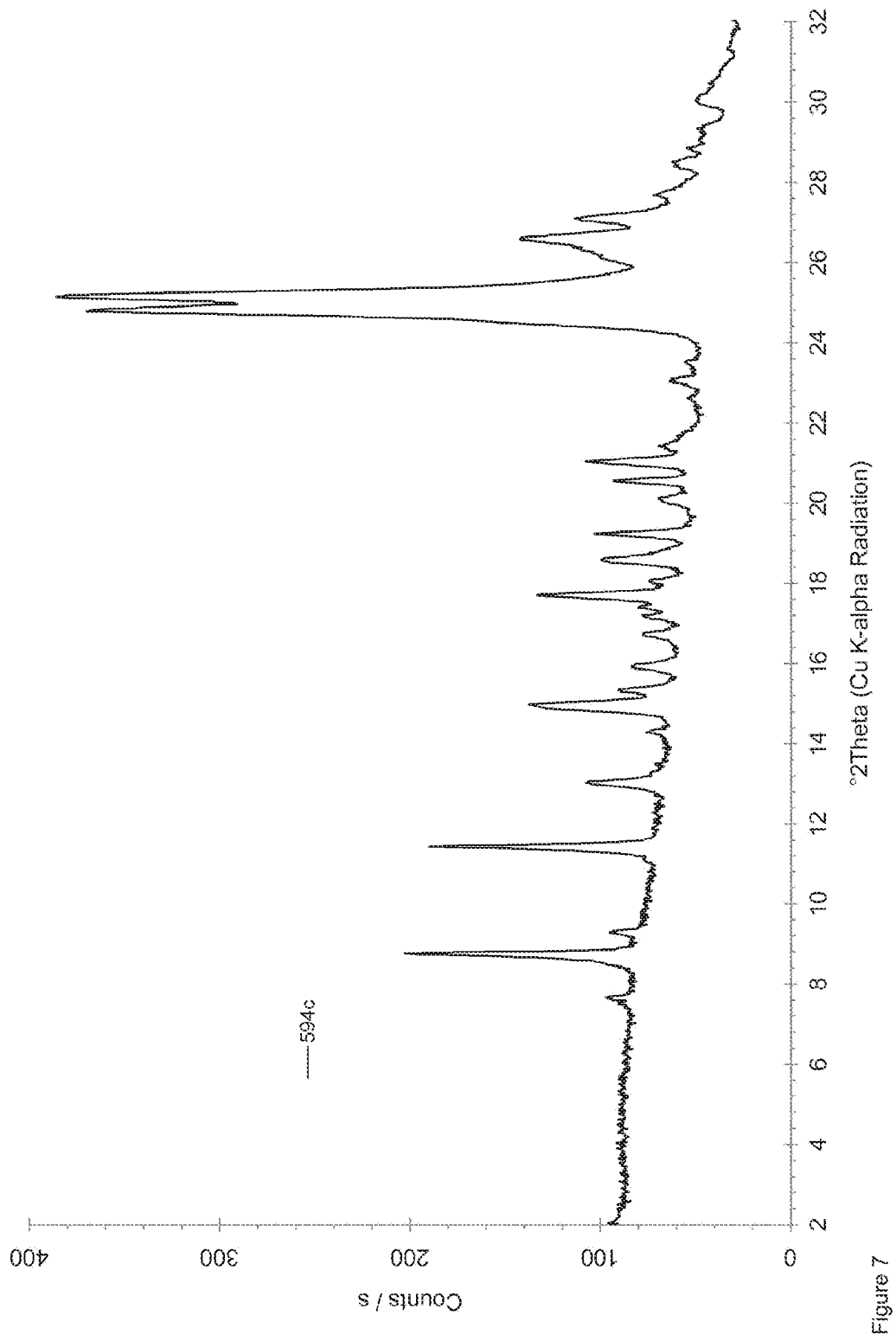
FIG. 7: Powder X-ray diffraction pattern of a nilotinib hydrochloride-gentisic acid hydrate co-crystal (form C).

Preparation of the Nilotinib Hydrochloride-gentisic Acid Co-crystal Form C 5.0 ml Water is added to 150 mg nilotinib hydrochloride-gentisic acid co-crystal form B according to example 12 and the obtained suspension is stirred at room temperature for 24 hours. Then the solid is filtered off and PXRD is performed. The product shows the PXRD pattern of nilotinib hydrochloride-gentisic acid co-crystal form C as depicted in FIG. 7 which shows peaks at positions as indicated in Table 13.

Example 16

Preparation of the Nilotinib Hydrochloride-gentisic Acid Co-crystal Form E

Figure 9:
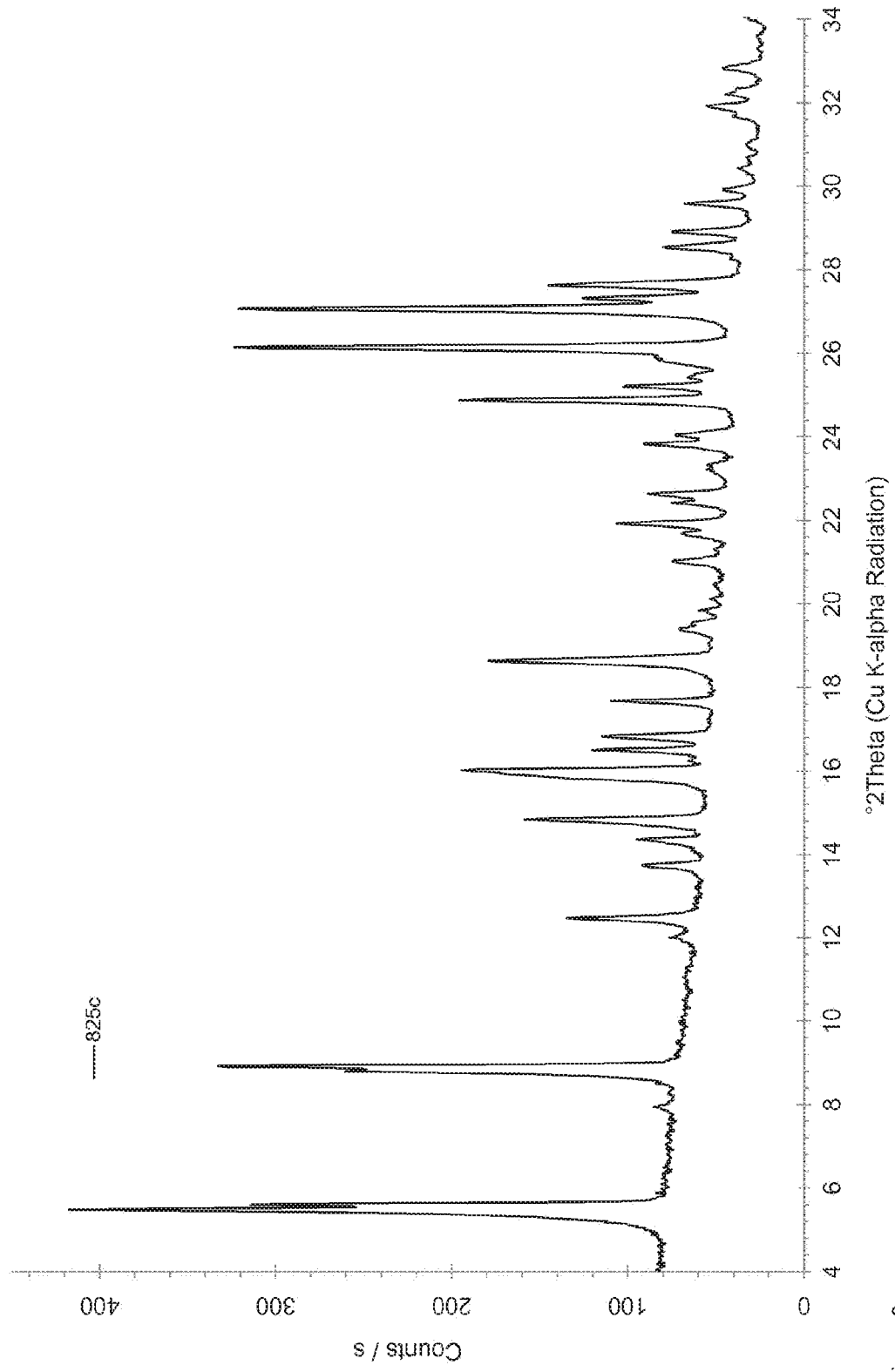
FIG. 9: Powder X-ray diffraction pattern of a nilotinib hydrochloride-gentisic acid co-crystal form E.

The non-dried solid material which corresponds to the nilotinib hydrochloride-gentisic acid co-crystal form B according to example 14 is kept in an open dish at room temperature at a relative humidity of about 25% for three days. Powder X-ray diffraction is carried out and the obtained PXRD pattern is designated as that of nilotinib hydrochloride-gentisic acid co-crystal form E as depicted in FIG. 9 which shows peaks at positions as indicated in Table 15. The elemental composition analysis revealed the following contents: 56.5% carbon, 4.4% hydrogen, 13.3% nitrogen, 13.6% oxygen, 7.7% fluorine, and 4.7% chloride.

This composition is consistent with a multicomponent crystal of the formula $C_{28}H_{22}F_3N_7O \cdot HCl \cdot C_7H_6O_4 \cdot 1.5H_2O$ and a molecular weight of 747.1 g/mol.

Example 17

Preparation of the Nilotinib Hydrochloride-gentisic Acid Co-crystal Form D

Figure 8:
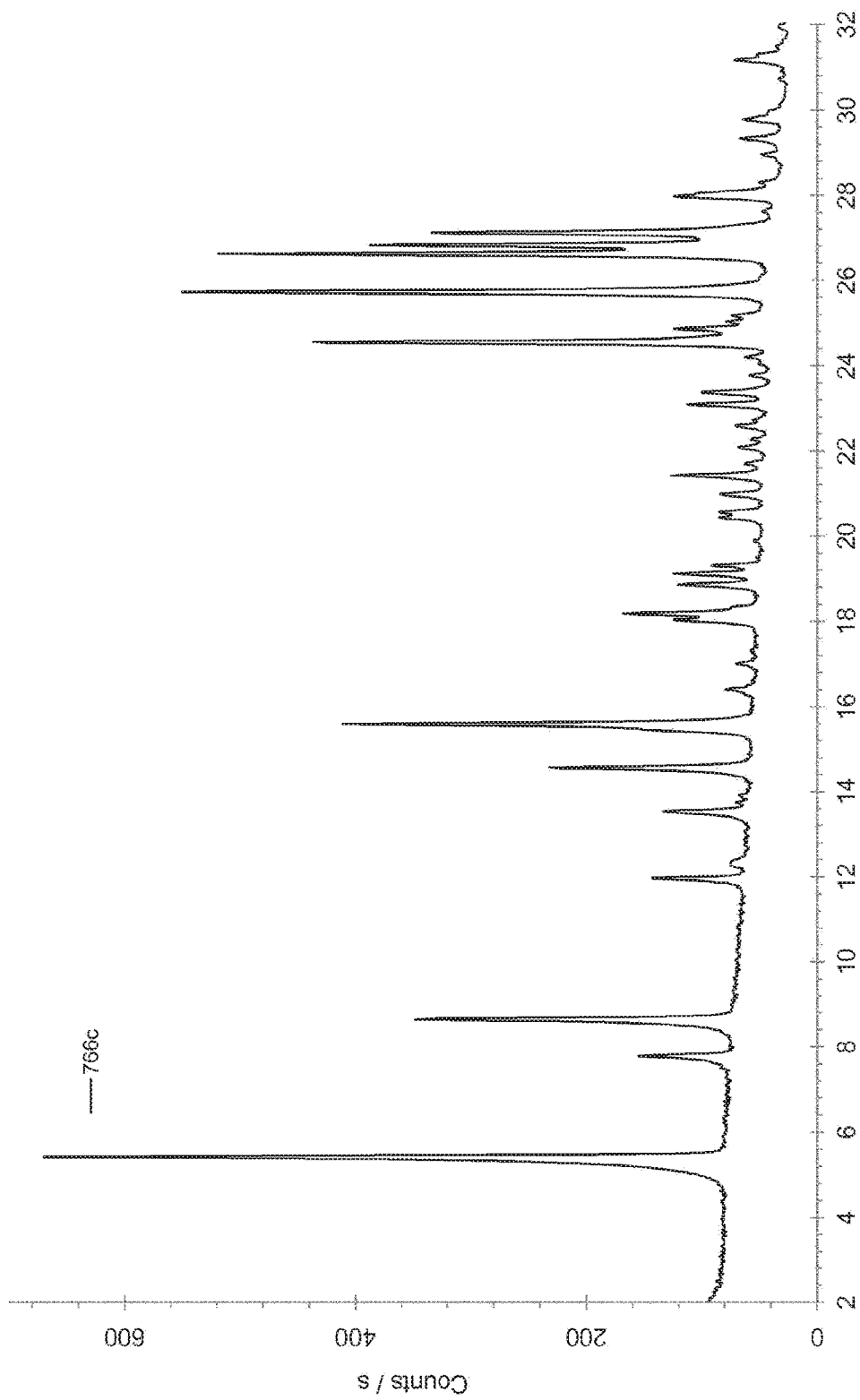
FIG. 8: Powder X-ray diffraction pattern of a nilotinib hydrochloride-gentisic acid co-crystal form D.

To 534 mg nilotinib free base (~1.0 mmol) is added 10.0 ml methanol, the obtained suspension is sonicated, heated to 65° C., and 0.55 ml of 2M aqueous hydrochloric acid and 161 mg gentisic acid (Fluka #37550) are added. After a clear solution is obtained, let the solution cool to room temperature and seeding with a few mg of nilotinib hydrochloride-gentisic acid co-crystal form A is carried out. A suspension forms which is stirred at room temperature overnight. Then the solid product is filtered off with a glass frit and the remaining amount in the reaction vessel (round glass flask) is recovered with 5 ml isopropanol and the dilute suspension with isopropanol is poured over the filter to wash, then the product on the glass frit is washed again with another 5 ml of isopropanol. Powder X-ray diffraction of the obtained crystalline material reveals a PXRD pattern that is designated as nilotinib hydrochloride-gentisic acid co-crystal form D as shown in FIG. 8 which shows peaks at positions as indicated in Table 14.

Example 18

Preparation of the Nilotinib Hydrochloride-isonicotinamide Co-crystal

Figure 10:
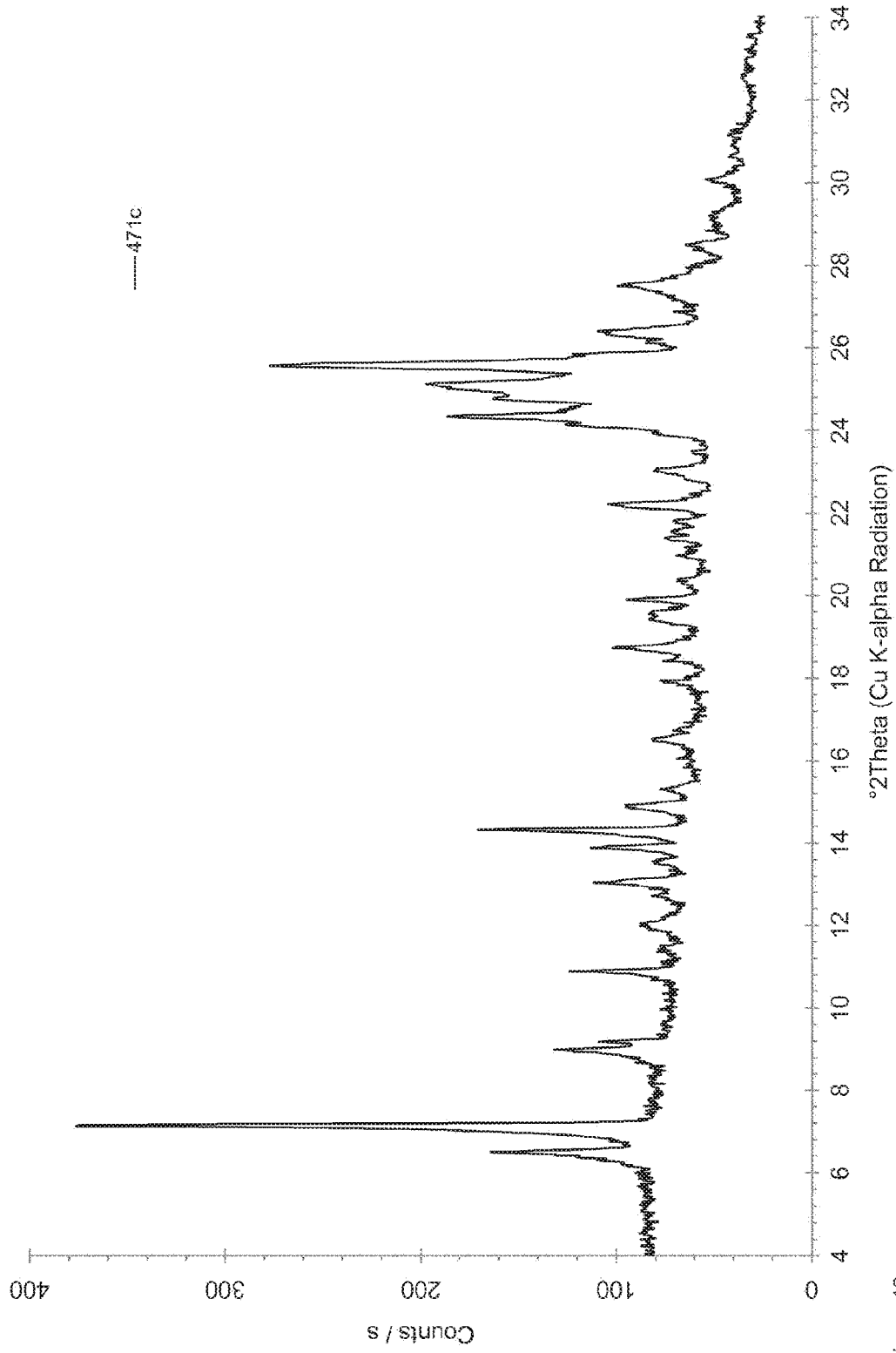
FIG. 10: Powder X-ray diffraction pattern of a nilotinib hydrochloride-isonicotinamide co-crystal.

To 275 mg nilotinib free base is added 10.0 ml methanol, the suspension is sonicated, heated to reflux temperature, and 280 microliter of 2M aqueous hydrochloric acid and 315 mg isonicotinamide (Aldrich #117451) is added. A clear solution is obtained, then the system is purged with a slight flow of nitrogen (about 5 ml/min), and the solution is allowed to cool to 30° C. and stirred for three days at this temperature. After about three days a suspension with a volume of about 4 ml is obtained from which the obtained solid product is separated by filtration. The co-crystalline material is dried under vacuum at room temperature overnight before powder X-ray diffraction and H-NMR spectroscopy is performed. H-NMR spectroscopy indicates a ratio of nilotinib free base to isonicotinamide of 1:0.75 and powder X-ray diffraction reveals a PXRD pattern as displayed in FIG. 10 which shows peaks at positions as indicated in Table 16.

Example 19

Preparation of the Nilotinib Hydrochloride-gallic Acid Methyl Ester Co-crystal

Figure 11:
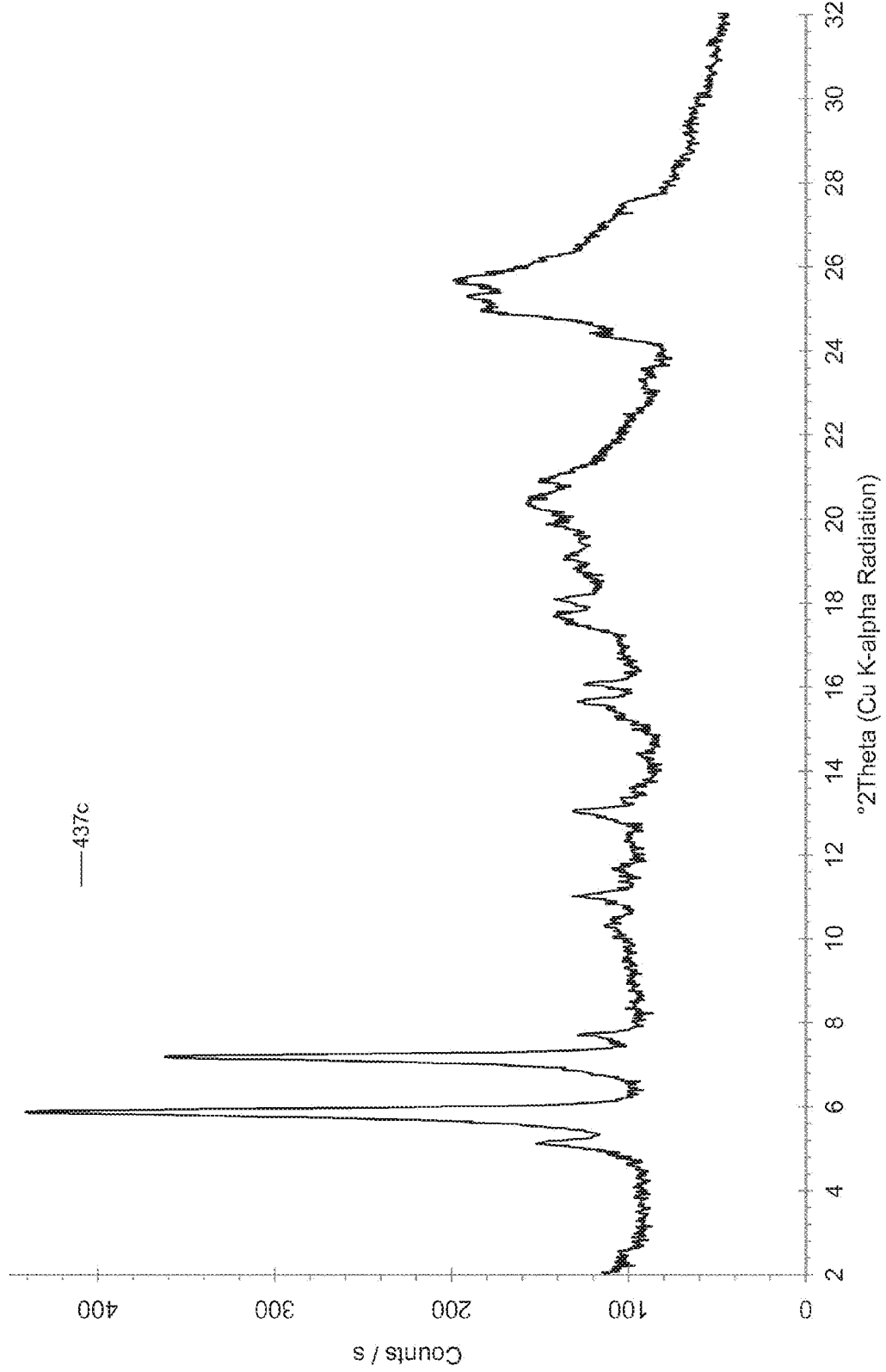
FIG. 11: Powder X-ray diffraction pattern of a nilotinib hydrochloride-gallic acid methyl ester co-crystal.

A 0.02M stock solution of nilotinib hydrochloride is prepared by dissolving 538 mg of nilotinib free base in 50.0 ml methanol with 167 µl 6M HCl. 10 ml of this stock solution is mixed with 4.0 ml of a stock solution (0.05M) of gallic acid methyl ester (Fluka #48690) in methanol. Then the solvent is slowly evaporated under nitrogen at a flow of about 50 ml per minute at room temperature. After evaporation of the methanol 4.0 ml isopropanol is added, the mixture is sonicated and stirred at 60° C., sonicated again, and then stirred at room temperature for several days before the crystalline product is separated by filtration. H-NMR spectroscopy indicates a ratio of nilotinib free base to gallic acid methyl ester of about 1:0.7 and powder X-ray diffraction reveals a PXRD pattern as displayed in FIG. 11 which shows peaks at positions as indicated in Table 17.

Example 20

Preparation of the Nilotinib-naphatalene Disulfonic Acid Co-crystal Form 1

Figure 12:
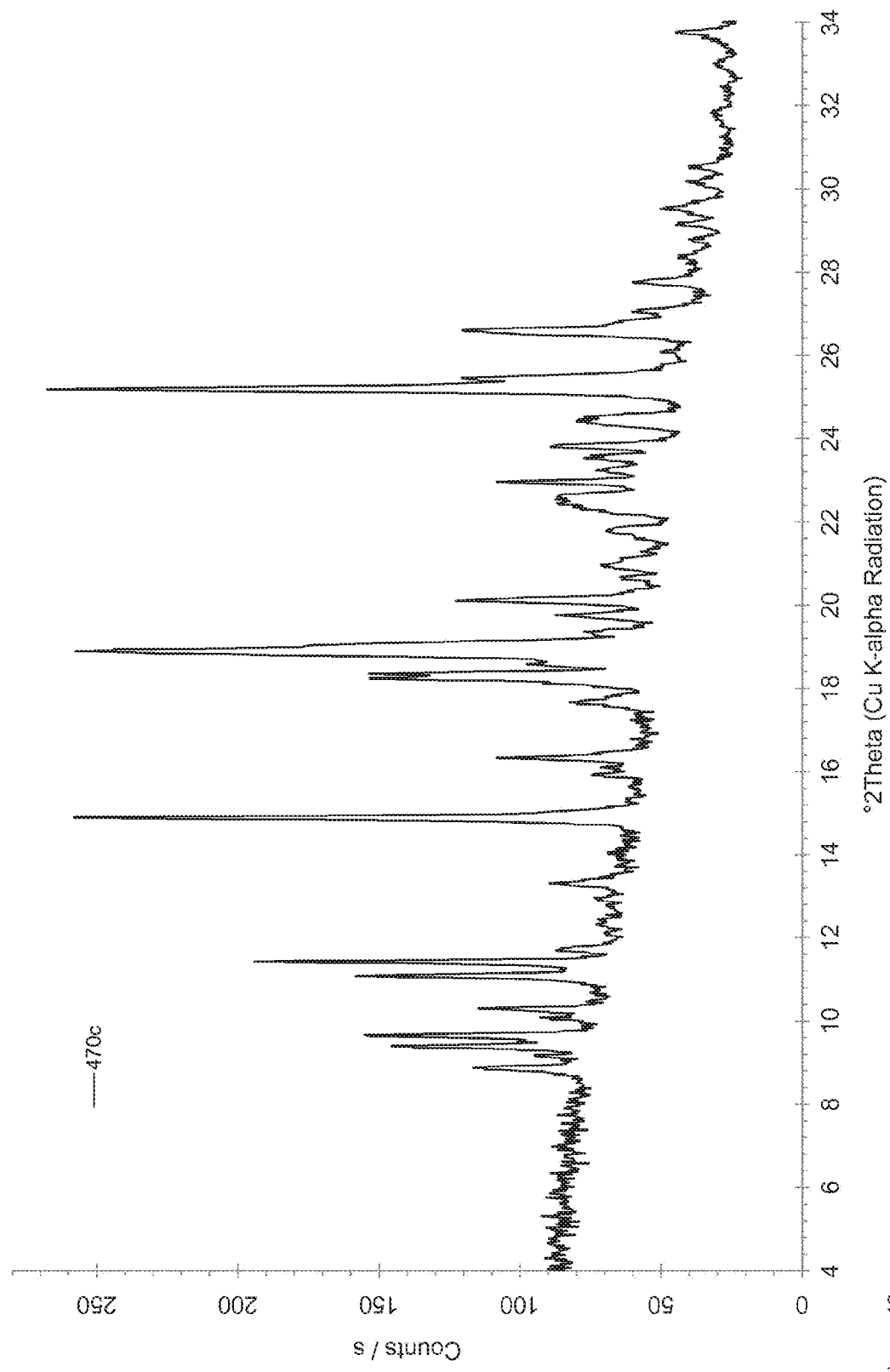
FIG. 12: Powder X-ray diffraction pattern of a nilotinib hydrochloride-naphthalene disulfonic acid co-crystal form 1.

To 265 mg nilotinib free base is added 10 ml of a 0.05M stock solution of naphthalene disulfonic acid in methanol and 260 microliter 2M HCl. This mixture is heated to reflux temperature; temporarily a solution is obtained from which a yellow precipitate is readily formed. The obtained suspension is stirred at 40° C. for about three hours while the system is purged with a slight flow with nitrogen (about 10 ml/min) until about 50% of the methanol is removed. Stirring is continued at room temperature for three days before the solid crystalline product is separated by filtration. H-NMR spectroscopy indicates a ratio of nilotinib free base to naphthalene disulfonic acid of about 1:1 and powder X-ray diffraction reveals a PXRD pattern as displayed in FIG. 12 which shows peaks at positions as indicated in Table 18.

Example 21

Preparation of the Nilotinib-naphatalene Disulfonic Acid Co-crystal Form 1b

Figure 13:
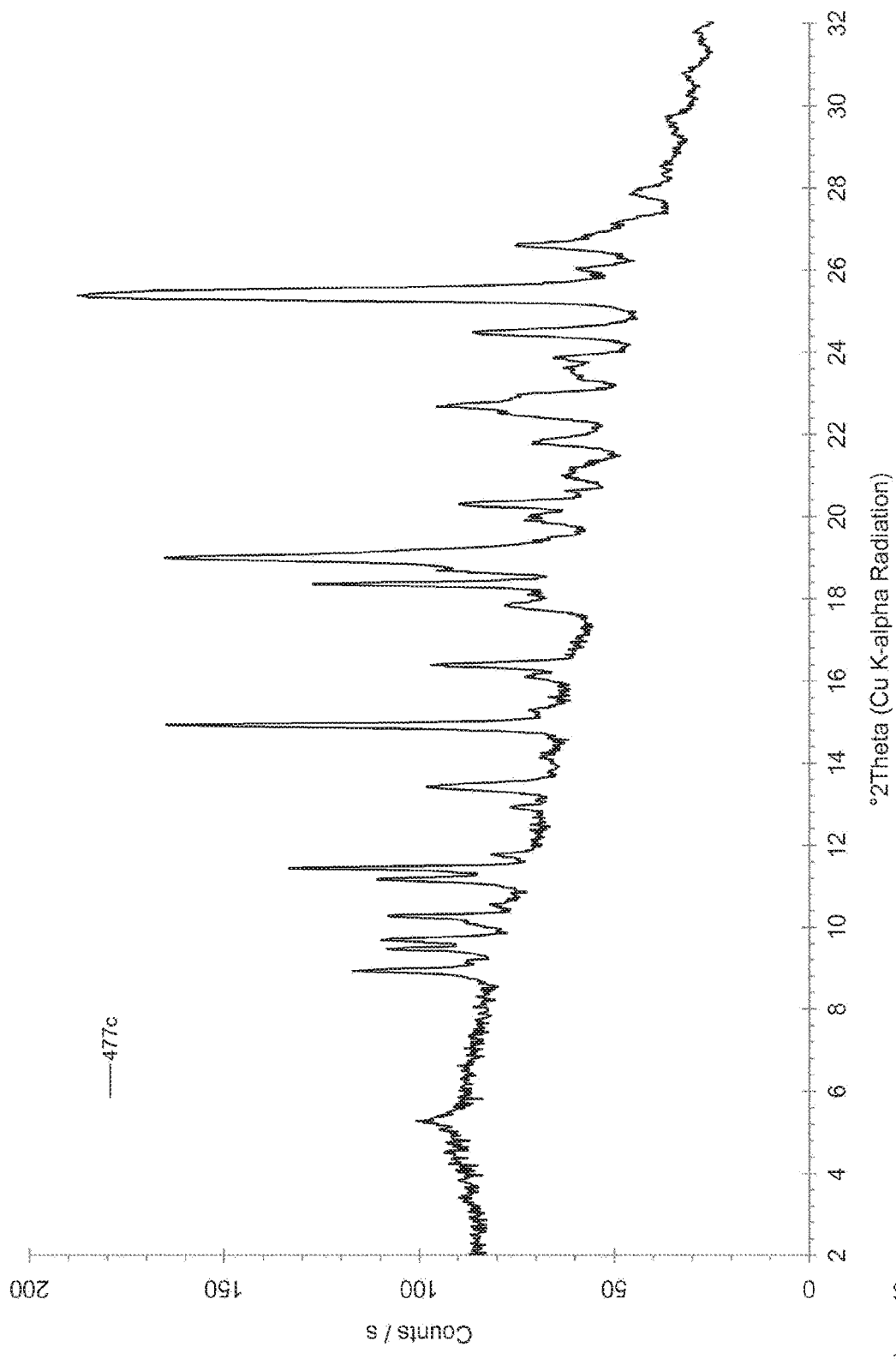
FIG. 13: Powder X-ray diffraction pattern of a nilotinib hydrochloride-naphthalene disulfonic acid co-crystal form 1 b.

To 266 mg nilotinib free base is added 145 mg naphthalene disulfonic acid (Merck #8.40104.0025), 10 ml methanol, and 260 µl 2N aqueous HCl solution. Dissolution is achieved by heating to reflux temperature. A suspension forms almost instantly which is stirred at 40° C. for two hours and at 30° C. for another two hours. Then the solid product is recovered by filtration and the obtained crystalline material is dried in air at r.t. H-NMR spectroscopy indicates a ratio of nilotinib free base to naphthalene disulfonic acid of about 1:1 and powder X-ray diffraction reveals a PXRD pattern as displayed in FIG. 13.

Example 22

Preparation of the Nilotinib Hydrochloride-naphatalene Disulfonic Acid Co-crystal Form 2

To 530 mg nilotinib free base is added 10 ml ethanol and 520 µl 2N HCl and then dissolution is achieved by heating to reflux temperature. To the hot solution is added 288 mg naphthalene disulfonic acid in form of a solution in 2.5 ml ethanol. A yellow precipitate forms almost immediately, if amorphous material is suspected, sonication is applied and seeding with a small amount of form 1 b according to example 21 is carried out. Temperature cycling is performed between 25 and 50° C. for six hours, then the mixture is stirred at ambient temperature while allowing some solvent to evaporate slowly through a small hole in the top of the glass vial (diameter about 5 mm) under ambient conditions. After about three days the obtained suspension is filtered and the solid co-crystalline product is dried in air at room temperature then several hours under vacuum at 50° C. Characterization by PXRD, TG-FTIR, and elemental composition analysis is performed. The result of the elemental composition analysis is shown in Table 19 is consistent with a multicomponent crystal of the formula $C_{28}H_{22}F_3N_7O \cdot 0.5 \cdot HCl \cdot 0.75 \cdot C_{10}H_8O_6S_2 \cdot H_2O$ with a molecular weight of 782.0 g/mol.

Figure 14:
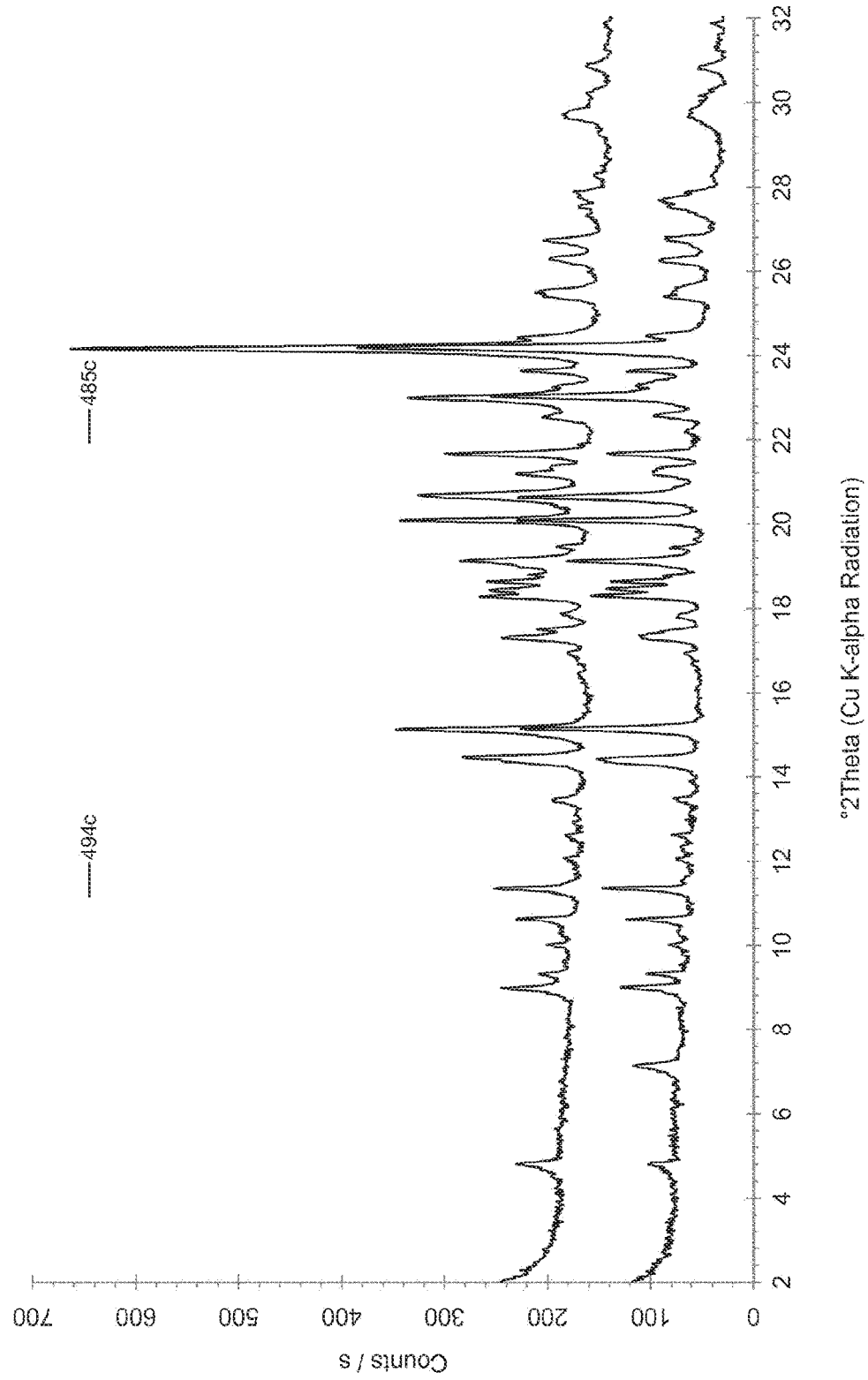
FIG. 14: Powder X-ray diffraction pattern of a nilotinib hydrochloride-naphthalene disulfonic acid co-crystal form 2 (lower trace) and form 2b (upper trace).

Powder X-ray diffraction reveals a PXRD pattern as displayed in FIG. 14 which shows peaks at positions as indicated in Table 20.

Example 23

Preparation of the Nilotinib Hydrochloride-naphatalene Disulfonic Acid Co-crystal Form 2b To 266 mg nilotinib free base is added 145 mg naphthalene disulfonic acid, 10 ml methanol, and 260 µl 2N aqueous HCl solution. Dissolution is achieved by heating to reflux temperature, but a suspension is readily obtained which is stirred at 40° C. for two hours and at 30° C. for another two hours. Then the solid product is recovered by filtration and the obtained co-crystalline material is dried in air at r.t. H-NMR spectroscopy indicates a ratio of nilotinib free base to naphthalene disulfonic acid of about 1:1 and powder X-ray diffraction reveals a PXRD pattern as displayed in FIG. 14.

Example 24

Preparation of the Nilotinib-naphatalene Disulfonic Acid Co-crystal Form 3

Figure 15:
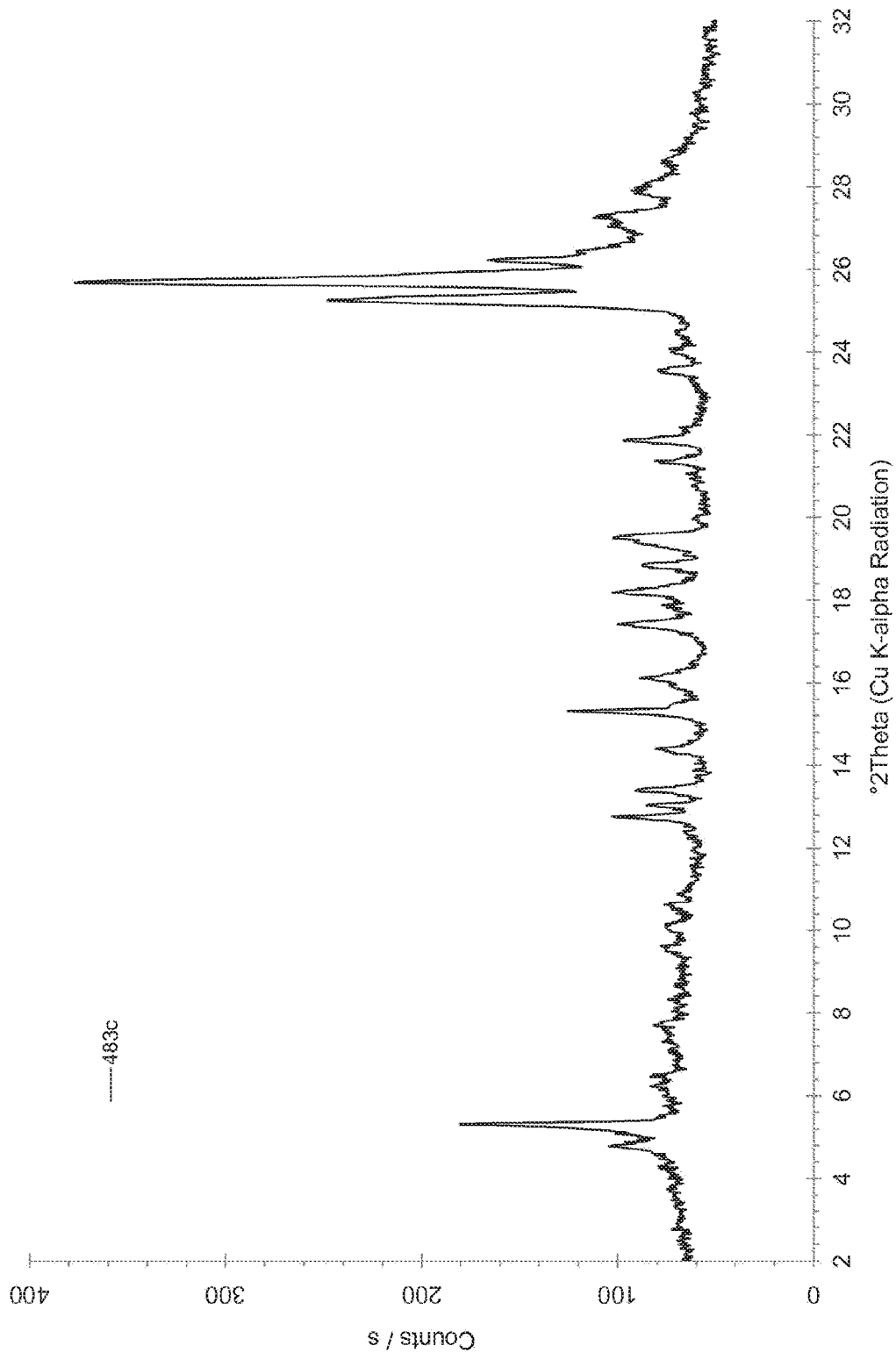
FIG. 15: Powder X-ray diffraction pattern of a nilotinib hydrochloride-naphthalene disulfonic acid co-crystal form 3.

To about 150 mg of the nilotinib-naphatalene disulfonic acid co-crystal form 1b according to example 21 is added 2 ml purified water and the obtained suspension is stirred at 25° C. for 2 hours. Then the solid product is recovered by filtration and the obtained material is dried in air at r.t. Investigation by powder X-ray diffraction reveals a PXRD pattern as displayed in FIG. 15 which shows peaks at positions as indicated in Table 21.

Example 25

Preparation of the Nilotinib-naphatalene Disulfonic Acid Co-crystal Form 4

Figure 16:
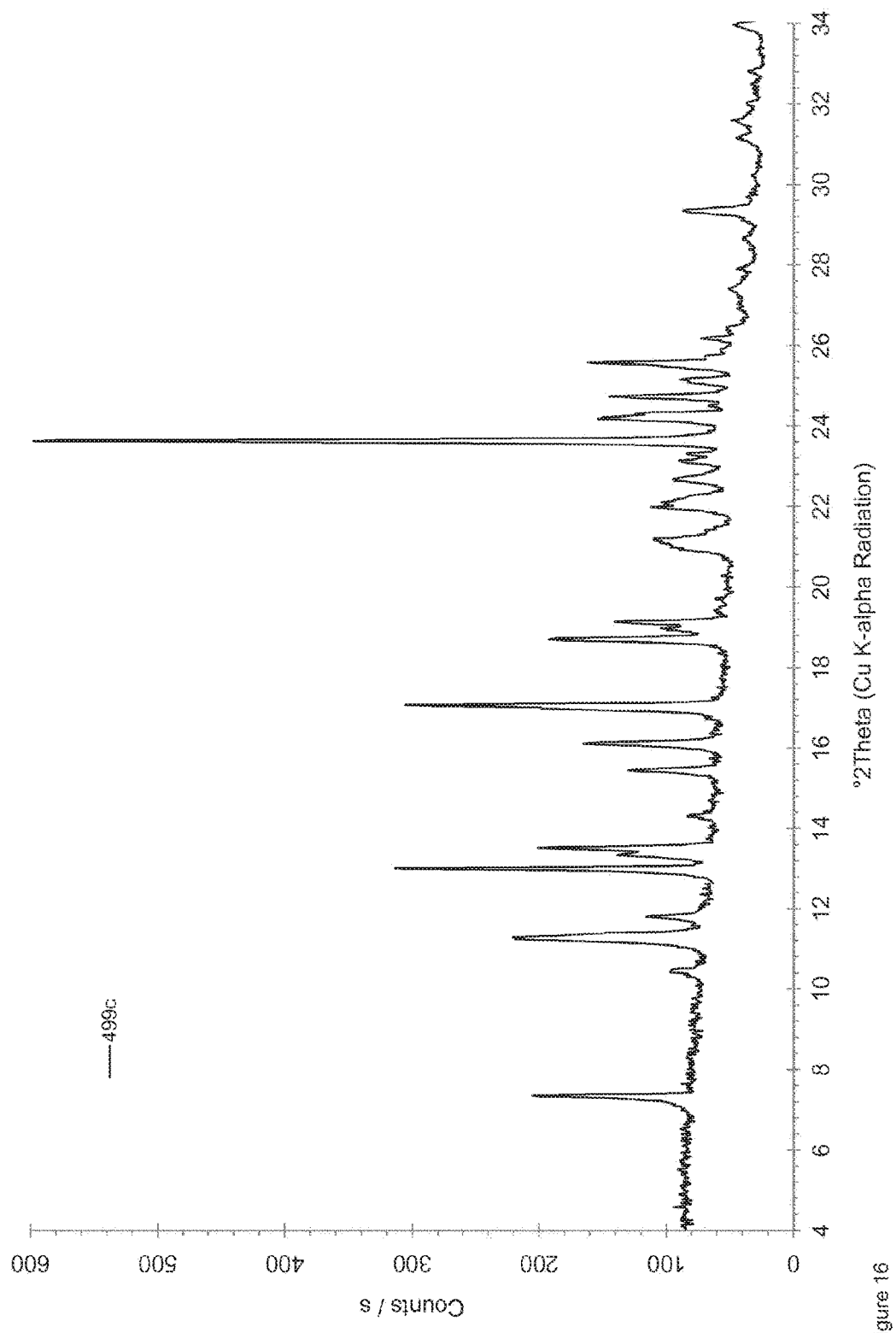
FIG. 16: Powder X-ray diffraction pattern of a nilotinib hydrochloride-naphthalene disulfonic acid co-crystal form 4.

To 265 mg nilotininb free base is added 6 ml ethanol, 260 µl 2N HCl, and 530 µl of a 0.5M stock solution of naphthalene disulfonic acid (0.5 eqs.) in ethanol and the mixture is heated to about 80° C., a yellow suspension is obtained which is then cooled to r.t. and stirred overnight. On the next day the solid sample is recovered by filtration and drying in air at r.t. before H-NMR spectroscopy and powder X-ray diffraction is performed. Investigation by powder X-ray diffraction reveals a PXRD pattern as displayed in FIG. 16 which shows peaks at positions as indicated in Table 22.

Example 26

Preparation of the Nilotinib-naphatalene Disulfonic Acid Co-crystal Form 5

Figure 17:
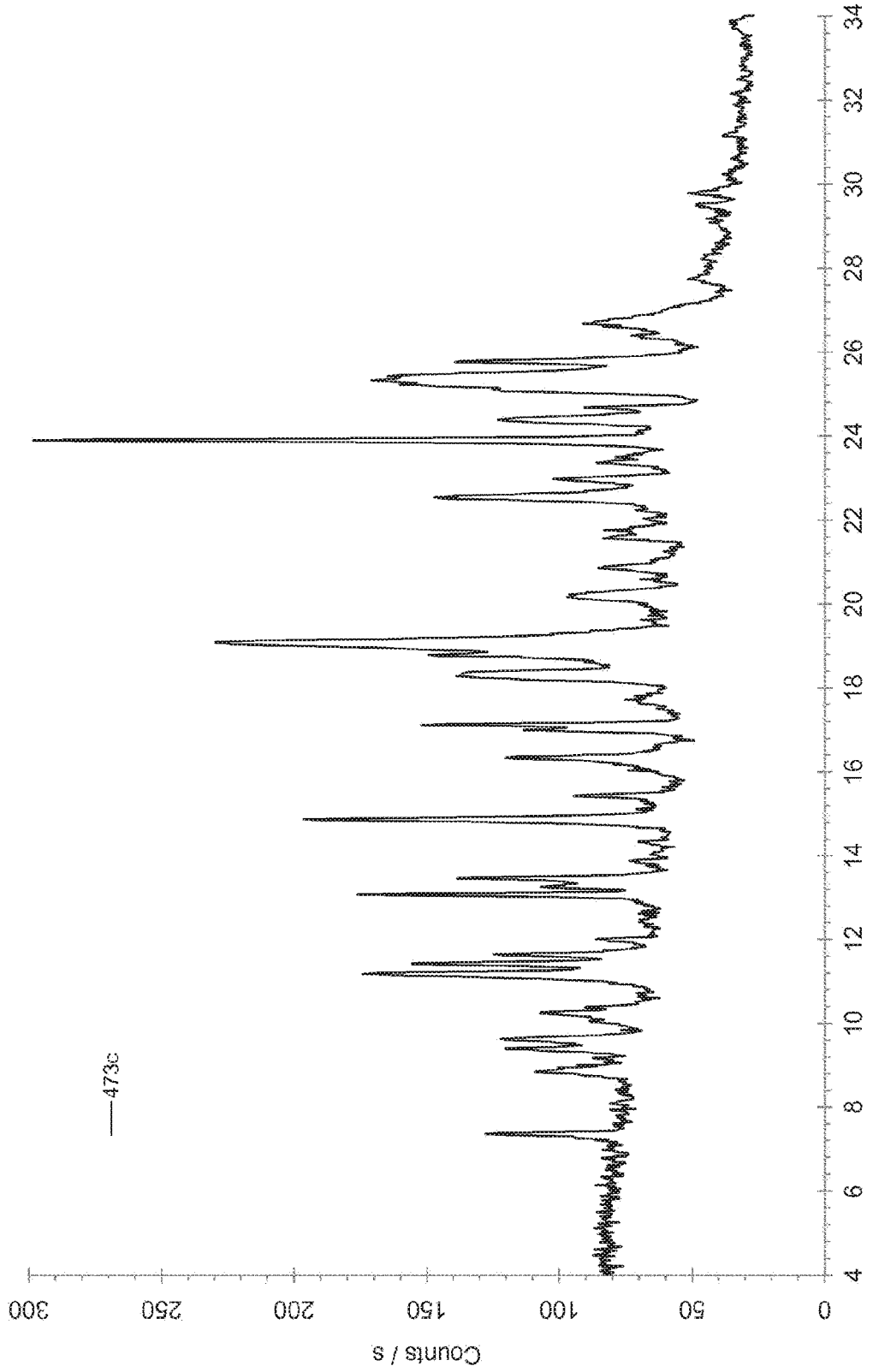
FIG. 17: Powder X-ray diffraction pattern of a nilotinib-naphthalene disulfonate co-crystal form 5.

To 265 mg nilotinib free base is added 145 mg naphthalene disulfonic acid and 5.0 ml methanol and mixture heated to reflux temperature. A suspension forms almost instantly which is then stirred and slowly cooled to r.t. After about an hour the yellowish suspension is filtered and the obtained solid dried in air at r.t. before H-NMR spectroscopy and powder X-ray diffraction is performed. Investigation by powder X-ray diffraction reveals a PXRD pattern as displayed in FIG. 17 which shows peaks at positions as indicated in Table 23. H-NMR reveals a ratio of nilotinib to naphthalene disulfonic acid of about 1:0.9.

Example 27

Preparation of the Nilotinib-naphatalene Disulfonic Acid Co-crystal Form 6

Figure 18:
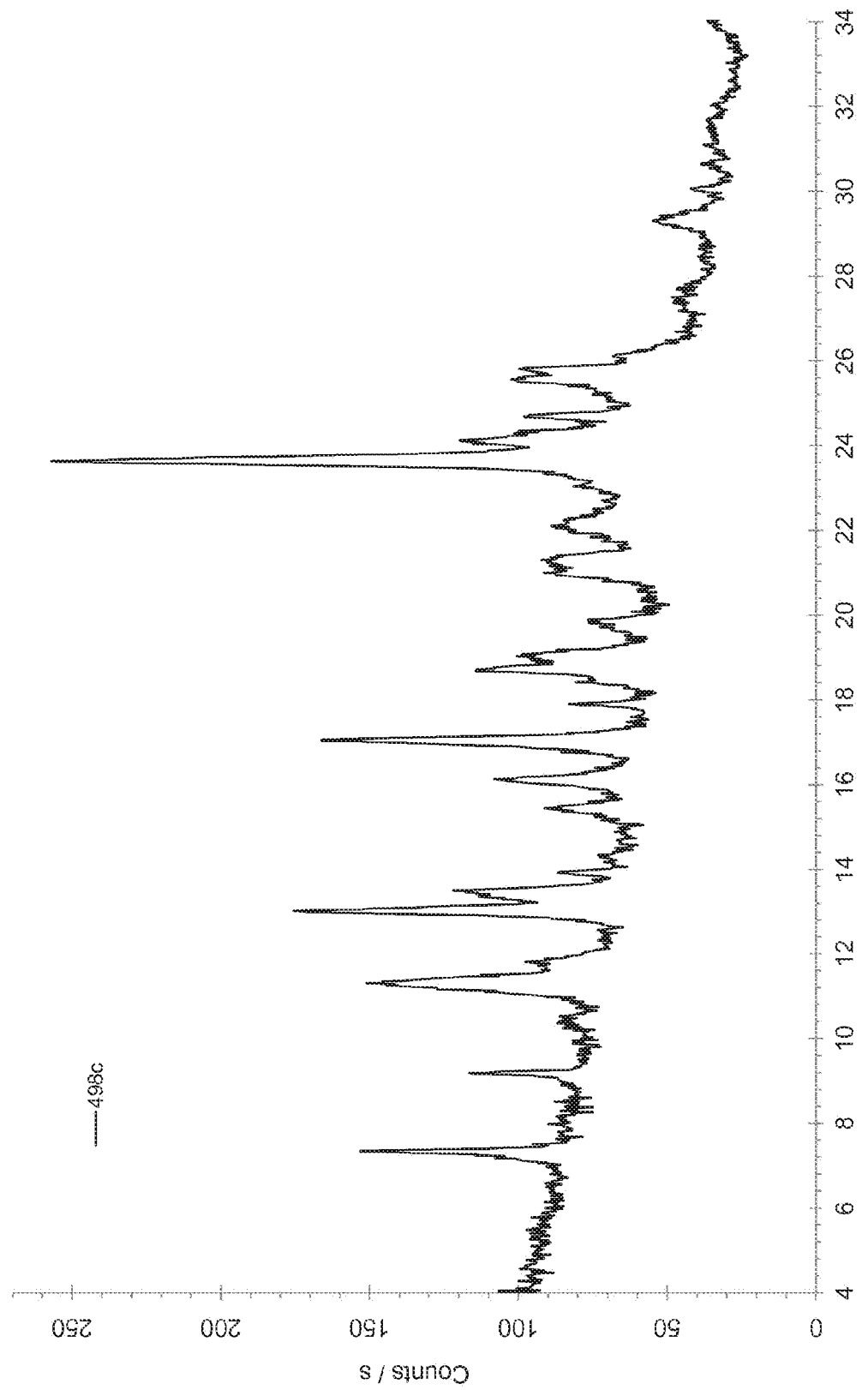
FIG. 18: Powder X-ray diffraction pattern of a nilotinib-naphthalene disulfonate co-crystal form 6.

To 265 mg nilotinib free base is added 6 ml ethanol, 500 µl 0.5M stock solution of naphthalene disulfonic acid in ethanol (0.5 eq.) and the mixture is heated to about 80° C., a yellow suspension is obtained which is then cooled to r.t. and stirred overnight. The solid sample is then recovered by filtration and drying in air at r.t. before H-NMR spectroscopy and powder X-ray diffraction is performed. Investigation by powder X-ray diffraction reveals a PXRD pattern as displayed in FIG. 18 which shows peaks at positions as indicated in Table 24. H-NMR reveals a ratio of nilotinib to naphthalene disulfonic acid of about 1:0.35.

Tables

TABLE 11

Powder X-ray diffraction 2Θ Angles, D-spacings, and qualitative relative intensities for the nilotinib hydrochloride - gentisic acid co-crystal form A.

| Angle °2 Θ | d value [Å] | Qualitative relative intensity |
|---|---|---|
| 5.5 | 16.2 | vs |
| 7.9 | 11.2 | m |
| 8.8 | 10.1 | s |
| 10.9 | 8.1 | m |
| 11.9 | 7.4 | m |
| 12.4 | 7.1 | m |
| 13.6 | 6.5 | m |
| 14.6 | 6.1 | s |
| 15.5 | 5.73 | w |
| 15.9 | 5.59 | s |
| 16.4 | 5.40 | m |
| 18.0 | 4.92 | m |
| 18.3 | 4.85 | m |
| 18.9 | 4.70 | m |
| 19.2 | 4.61 | m |
| 20.5 | 4.33 | w |
| 20.9 | 4.24 | w |
| 21.7 | 4.09 | m |
| 22.6 | 3.93 | w |
| 23.1 | 3.84 | m |
| 23.6 | 3.76 | w |
| 24.2 | 3.68 | w |
| 24.7 | 3.61 | s |
| 25.0 | 3.56 | m |
| 25.8 | 3.45 | s |
| 26.8 | 3.33 | s |
| 26.9 | 3.31 | s |
| 27.2 | 3.27 | s |
| 27.5 | 3.24 | w |
| 28.1 | 3.17 | m |

TABLE 12

Powder X-ray diffraction 2Θ Angles, D-spacings, and qualitative relative intensities for the nilotinib hydrochloride - gentisic acid co-crystal form B.

| Angle °2 Θ | d value [Å] | Qualitative relative intensity |
|---|---|---|
| 5.5 | 16.1 | vs |
| 7.9 | 11.2 | m |
| 8.8 | 10.1 | s |
| 12.1 | 7.3 | m |
| 12.5 | 7.1 | w |
| 13.7 | 6.5 | w |
| 14.1 | 6.3 | w |
| 14.7 | 6.0 | m |
| 15.8 | 5.60 | s |
| 16.3 | 5.44 | w |
| 16.6 | 5.33 | w |
| 17.2 | 5.14 | w |
| 18.4 | 4.82 | m |
| 19.1 | 4.65 | w |
| 19.4 | 4.58 | w |
| 19.6 | 4.53 | w |
| 20.1 | 4.41 | w |
| 20.7 | 4.29 | w |
| 21.3 | 4.18 | w |
| 21.7 | 4.09 | w |
| 22.4 | 3.97 | w |
| 22.9 | 3.88 | w |
| 23.4 | 3.80 | m |
| 23.7 | 3.75 | w |
| 24.8 | 3.58 | s |
| 25.1 | 3.54 | w |
| 26.0 | 3.42 | s |
| 26.9 | 3.31 | s |
| 27.1 | 3.28 | s |
| 27.4 | 3.25 | m |
| 28.3 | 3.15 | w |
| 29.3 | 3.05 | w |
| 29.7 | 3.01 | w |

TABLE 13

Powder X-ray diffraction 2Θ Angles, D-spacings, and qualitative relative intensities for the nilotinib hydrochloride - gentisic acid co-crystal form C.

| Angle °2 Θ | d value [Å] | Qualitative relative intensity |
|---|---|---|
| 7.7 | 11.5 | m |
| 8.7 | 10.1 | s |
| 9.3 | 9.5 | m |
| 11.4 | 7.7 | s |
| 13.0 | 6.8 | m |
| 13.3 | 6.7 | m |
| 14.3 | 6.2 | w |
| 14.9 | 5.93 | s |
| 15.3 | 5.79 | m |
| 15.9 | 5.57 | m |
| 16.7 | 5.31 | m |
| 17.2 | 5.16 | m |
| 17.7 | 5.02 | s |
| 18.0 | 4.92 | m |
| 18.5 | 4.78 | m |
| 19.2 | 4.62 | m |
| 20.0 | 4.43 | m |
| 20.6 | 4.32 | m |
| 21.0 | 4.23 | m |
| 21.4 | 4.15 | m |
| 23.1 | 3.86 | m |
| 24.4 | 3.64 | m |
| 24.7 | 3.60 | vs |
| 25.1 | 3.55 | vs |
| 26.3 | 3.39 | m |
| 26.5 | 3.36 | s |
| 27.0 | 3.30 | s |
| 27.7 | 3.22 | m |
| 28.4 | 3.14 | m |
| 29.3 | 3.05 | m |
| 30.0 | 2.98 | m |
| 30.4 | 2.94 | m |

TABLE 14

Powder X-ray diffraction 2Θ Angles, D-spacings, and qualitative relative intensities for the nilotinib hydrochloride - gentisic acid co-crystal form D.

| Angle °2 Θ | d value [Å] | Qualitative relative intensity |
|---|---|---|
| 5.4 | 16.3 | vs |
| 7.8 | 11.4 | m |
| 8.6 | 10.2 | s |
| 12.0 | 7.4 | m |
| 12.3 | 7.2 | w |
| 13.5 | 6.5 | m |
| 14.5 | 6.1 | s |
| 15.6 | 5.68 | s |
| 16.4 | 5.40 | w |
| 17.0 | 5.21 | w |
| 18.0 | 4.91 | m |
| 18.2 | 4.88 | m |
| 18.9 | 4.70 | m |
| 19.1 | 4.64 | m |
| 19.3 | 4.60 | w |
| 20.4 | 4.35 | w |

TABLE 14-continued

Powder X-ray diffraction 2Θ Angles, D-spacings, and qualitative relative intensities for the nilotinib hydrochloride - gentisic acid co-crystal form D.

| Angle °2 Θ | d value [Å] | Qualitative relative intensity |
|---|---|---|
| 21.0 | 4.23 | w |
| 21.4 | 4.14 | m |
| 22.1 | 4.02 | w |
| 22.6 | 3.93 | w |
| 23.1 | 3.85 | m |
| 23.4 | 3.80 | w |
| 23.8 | 3.74 | w |
| 24.2 | 3.67 | w |
| 24.5 | 3.62 | s |
| 24.9 | 3.58 | m |
| 25.7 | 3.46 | vs |
| 26.6 | 3.35 | vs |
| 26.8 | 3.32 | s |
| 27.1 | 3.29 | s |
| 28.0 | 3.19 | m |
| 28.9 | 3.08 | w |
| 29.3 | 3.04 | w |

TABLE 15

Powder X-ray diffraction 2Θ Angles, D-spacings, and qualitative relative intensities for the nilotinib hydrochloride - gentisic acid co-crystal form E.

| Angle °2 Θ | d value [Å] | Qualitative relative intensity |
|---|---|---|
| 5.5 | 16.2 | vs |
| 5.6 | 15.8 | vs |
| 7.9 | 11.1 | m |
| 8.9 | 9.9 | vs |
| 12.0 | 7.4 | m |
| 12.4 | 7.1 | s |
| 13.7 | 6.4 | m |
| 14.4 | 6.2 | m |
| 14.8 | 5.97 | s |
| 16.0 | 5.53 | s |
| 16.5 | 5.37 | m |
| 16.8 | 5.26 | m |
| 17.7 | 5.02 | m |
| 18.6 | 4.76 | s |
| 19.4 | 4.58 | m |
| 21.0 | 4.23 | m |
| 21.7 | 4.09 | m |
| 21.9 | 4.05 | m |
| 22.4 | 3.96 | m |
| 22.6 | 3.93 | m |
| 23.2 | 3.83 | w |
| 23.8 | 3.73 | m |
| 24.0 | 3.70 | m |
| 24.9 | 3.58 | s |
| 25.2 | 3.53 | m |
| 25.9 | 3.44 | m |
| 26.1 | 3.41 | vs |
| 27.1 | 3.29 | vs |
| 27.3 | 3.26 | s |
| 27.6 | 3.23 | s |
| 28.5 | 3.13 | m |
| 28.9 | 3.09 | m |
| 29.6 | 3.02 | m |

TABLE 16

Powder X-ray diffraction 2Θ Angles, D-spacings, and qualitative relative intensities for co-crystal of nilotinib hydrochloride with isonicotinamide.

| Angle °2 Θ | d value [Å] | Qualitative relative intensity |
|---|---|---|
| 6.5 | 13.6 | s |
| 7.1 | 12.4 | vs |
| 9.0 | 9.8 | m |
| 9.2 | 9.6 | m |
| 10.9 | 8.1 | m |
| 12.0 | 7.3 | w |
| 13.1 | 6.8 | m |
| 13.9 | 6.4 | m |
| 14.3 | 6.2 | s |
| 14.9 | 5.94 | m |
| 15.3 | 5.78 | w |
| 16.5 | 5.37 | w |
| 17.9 | 4.95 | w |
| 18.7 | 4.73 | m |
| 19.4 | 4.57 | w |
| 19.9 | 4.46 | m |
| 21.4 | 4.15 | w |
| 22.2 | 4.00 | m |
| 23.0 | 3.86 | w |
| 24.1 | 3.68 | m |
| 24.3 | 3.65 | s |
| 24.8 | 3.59 | s |
| 25.1 | 3.54 | s |
| 25.6 | 3.48 | vs |
| 25.8 | 3.45 | m |
| 26.4 | 3.38 | m |
| 27.5 | 3.24 | m |

TABLE 17

Powder X-ray diffraction 2Θ Angles, D-spacings, and qualitative relative intensities for the co-crystal of nilotinib hydrochloride with gallic acid methyl ester.

| Angle °2 Θ | d value [Å] | Qualitative relative intensity |
|---|---|---|
| 5.1 | 17.2 | s |
| 5.9 | 15.0 | vs |
| 7.2 | 12.3 | vs |
| 7.7 | 11.5 | m |
| 11.0 | 8.0 | m |
| 13.1 | 6.8 | m |
| 15.7 | 5.66 | m |
| 16.1 | 5.51 | m |
| 17.7 | 5.01 | s |
| 18.1 | 4.90 | s |
| 19.9 | 4.46 | s |
| 20.4 | 4.36 | s |
| 20.9 | 4.25 | s |
| 24.4 | 3.65 | m |
| 25.0 | 3.56 | s |
| 25.7 | 3.46 | s |

TABLE 18

Powder X-ray diffraction 2Θ Angles, D-spacings, and qualitative relative intensities for the nilotinib - naphthalene disulfonic acid co-crystal form 1.

| Angle °2 Θ | d value [Å] | Qualitative relative intensity |
|---|---|---|
| 8.9 | 10.0 | m |
| 9.4 | 9.4 | s |
| 9.7 | 9.2 | s |
| 10.3 | 8.6 | m |
| 11.1 | 8.0 | s |
| 11.4 | 7.7 | vs |
| 14.9 | 5.95 | vs |
| 16.3 | 5.42 | s |

TABLE 18-continued

Powder X-ray diffraction 2Θ Angles, D-spacings, and qualitative relative intensities for the nilotinib - naphthalene disulfonic acid co-crystal form 1.

| Angle °2 Θ | d value [Å] | Qualitative relative intensity |
|---|---|---|
| 17.7 | 5.01 | s |
| 18.3 | 4.83 | s |
| 18.9 | 4.69 | vs |
| 19.8 | 4.49 | m |
| 20.1 | 4.41 | m |
| 23.0 | 3.87 | m |
| 23.8 | 3.73 | m |
| 24.4 | 3.64 | m |
| 25.2 | 3.53 | vs |
| 25.4 | 3.50 | s |
| 26.6 | 3.35 | s |

TABLE 19

Elemental composition analysis result for the nilotinib hydrochloride - naphthalene disulfonic acid co-crystal form 2a.

| Element | % Found | % Expected |
|---|---|---|
| C | 54.5 | 54.53 |
| H | 4.1 | 3.93 |
| N | 12.4 | 12.54 |
| O | 13.1 | 13.30 |
| F | 7.2 | 7.29 |
| Cl | 2.0 | 2.27 |
| S | 6.5 | 6.15 |

TABLE 10

Powder X-ray diffraction 2Θ Angles, D-spacings, and qualitative relative intensities for the nilotinib hydrochloride - naphthalene disulfonic acid co-crystal form 2.

| Angle °2 Θ | d value [Å] | Qualitative relative intensity |
|---|---|---|
| 4.8 | 18.4 | w |
| 9.0 | 9.9 | w |
| 9.3 | 9.5 | w |
| 10.6 | 8.3 | w |
| 11.4 | 7.8 | m |
| 13.5 | 6.6 | w |
| 14.5 | 6.1 | m |
| 15.1 | 5.86 | m |
| 17.3 | 5.12 | w |
| 18.3 | 4.85 | m |
| 18.4 | 4.81 | m |
| 18.6 | 4.76 | m |
| 19.1 | 4.63 | m |
| 19.5 | 4.56 | vw |
| 20.1 | 4.42 | m |
| 20.7 | 4.29 | m |
| 21.2 | 4.19 | w |
| 21.7 | 4.10 | m |
| 22.5 | 3.94 | w |
| 23.0 | 3.87 | m |
| 23.3 | 3.82 | w |
| 23.6 | 3.76 | w |
| 24.2 | 3.68 | vs |
| 24.4 | 3.64 | w |
| 25.5 | 3.49 | w |
| 26.3 | 3.39 | w |
| 26.7 | 3.33 | w |

TABLE 11

Powder X-ray diffraction 2Θ Angles, D-spacings, and qualitative relative intensities of for the nilotinib - naphthalene disulfonic acid co-crystal form 3.

| Angle °2 Θ | d value [Å] | Qualitative relative intensity |
|---|---|---|
| 4.8 | 18.5 | m |
| 5.3 | 16.6 | s |
| 6.5 | 13.6 | w |
| 7.7 | 11.4 | w |
| 9.6 | 9.2 | w |
| 10.1 | 8.8 | w |
| 10.6 | 8.3 | w |
| 12.8 | 6.9 | m |
| 13.0 | 6.8 | w |
| 13.4 | 6.6 | w |
| 14.4 | 6.2 | w |
| 15.3 | 5.78 | m |
| 16.1 | 5.50 | w |
| 17.4 | 5.09 | m |
| 17.8 | 4.97 | w |
| 18.2 | 4.87 | m |
| 18.8 | 4.71 | w |
| 19.5 | 4.54 | m |
| 21.3 | 4.16 | w |
| 21.9 | 4.06 | m |
| 23.6 | 3.77 | w |
| 24.0 | 3.70 | w |
| 25.3 | 3.52 | s |
| 25.7 | 3.46 | vs |
| 26.2 | 3.40 | s |
| 27.3 | 3.27 | m |

TABLE 12

Powder X-ray diffraction 2Θ Angles, D-spacings, and qualitative relative intensities of for the nilotinib - naphthalene disulfonic acid co-crystal form 4.

| Angle °2 Θ | d value [Å] | Qualitative relative intensity |
|---|---|---|
| 7.3 | 12.0 | m |
| 10.5 | 8.4 | w |
| 11.3 | 7.9 | m |
| 11.8 | 7.5 | w |
| 13.0 | 6.8 | s |
| 13.4 | 6.6 | w |
| 13.5 | 6.6 | m |
| 14.3 | 6.2 | vw |
| 15.5 | 5.73 | w |
| 16.1 | 5.50 | m |
| 17.1 | 5.20 | s |
| 18.7 | 4.74 | m |
| 19.0 | 4.67 | w |
| 19.1 | 4.63 | w |
| 21.0 | 4.23 | w |
| 21.2 | 4.20 | w |
| 22.0 | 4.04 | w |
| 22.1 | 4.02 | w |
| 22.2 | 3.99 | vw |
| 22.7 | 3.92 | w |
| 23.1 | 3.84 | w |
| 23.3 | 3.82 | vw |
| 23.6 | 3.76 | vs |
| 24.2 | 3.68 | m |
| 24.7 | 3.60 | w |
| 25.1 | 3.54 | w |
| 25.6 | 3.48 | m |

TABLE 13

Powder X-ray diffraction 2Θ Angles, D-spacings, and qualitative relative intensities of for the nilotinib naphthalene disulfonate salt form 5.

| Angle °2 Θ | d value [Å] | Qualitative relative intensity |
| --- | --- | --- |
| 7.4 | 12.0 | M |
| 8.9 | 10.0 | M |
| 9.4 | 9.4 | M |
| 9.6 | 9.2 | M |
| 10.3 | 8.6 | M |
| 10.4 | 8.5 | M |
| 11.2 | 7.9 | S |
| 11.4 | 7.7 | S |
| 11.6 | 7.6 | M |
| 12.0 | 7.4 | M |
| 13.1 | 6.8 | S |
| 13.3 | 6.7 | M |
| 13.5 | 6.6 | S |
| 13.9 | 6.4 | W |
| 14.3 | 6.2 | W |
| 14.9 | 6.0 | S |
| 15.4 | 5.74 | M |
| 16.3 | 5.42 | M |
| 17.0 | 5.21 | M |
| 17.1 | 5.17 | S |
| 17.7 | 5.00 | M |
| 18.3 | 4.84 | S |
| 18.8 | 4.72 | S |
| 19.1 | 4.65 | Vs |
| 20.2 | 4.40 | M |
| 20.9 | 4.25 | M |
| 21.6 | 4.11 | M |
| 21.8 | 4.08 | M |
| 22.5 | 3.94 | S |
| 23.0 | 3.87 | M |
| 23.4 | 3.80 | M |
| 23.9 | 3.72 | Vs |
| 24.4 | 3.65 | M |
| 24.7 | 3.61 | M |

TABLE 14

Powder X-ray diffraction 2Θ Angles, D-spacings, and qualitative relative intensities of for the nilotinib naphthalene disulfonate salt form 6.

| Angle °2 Θ | d value [Å] | Qualitative relative intensity |
| --- | --- | --- |
| 7.3 | 12.0 | M |
| 9.2 | 9.6 | M |
| 11.3 | 7.8 | M |
| 13.0 | 6.8 | S |
| 13.5 | 6.6 | M |
| 13.9 | 6.4 | W |
| 15.4 | 5.73 | W |
| 16.1 | 5.50 | W |
| 17.1 | 5.20 | M |
| 17.9 | 4.95 | W |
| 18.7 | 4.74 | W |
| 19.0 | 4.66 | W |
| 21.3 | 4.17 | W |
| 22.1 | 4.02 | W |
| 23.6 | 3.76 | Vs |
| 24.1 | 3.69 | M |
| 24.7 | 3.60 | W |
| 25.6 | 3.48 | W |
| 25.8 | 3.45 | W |

The invention claimed is:

1. A crystalline material, comprising a co-crystal of component (a) and component (b), wherein:
   (a) a hydrohalogenide salt of nilotinib, or a mixture of nilotinib and a hydrohalogenide salt of nilotinib; and
   (b) a carboxylic acid, carboxylic acid ester, carboxylic acid amide, or sulfonic acid.

2. A crystalline material comprising a co-crystal of component (a) and component (b), wherein:
   (a) a hydrohalogenide salt of nilotinib; and
   (b) a carboxylic acid.

3. The crystalline material according to claim 1, wherein component (a) is a hydrochloride salt of nilotinib.

4. The crystalline material according to claim 1, wherein component (b) is a carboxylic acid.

5. The crystalline material according to claim 1, wherein a molar ratio of component (a) and component (b) is from about 2:1 to about 1:2.

6. The crystalline material according to claim 1, wherein (b) is fumaric acid, and the crystalline material has a powder X-ray diffraction pattern with the characteristic peaks expressed in d-values(Å): 13.6, 7.1, 5.68, 4.84, 4.67, 4.57, 3.87, 3.69, 3.39, 3.36, 3.31, and 3.16.

7. The crystalline material according to claim 1, wherein (b) is maleic acid, and the crystalline material has a powder X-ray diffraction pattern with the following characteristic peaks expressed in d-values (Å):
   a) 17.2, 15.8, 10.8, 9.1, 7.3, 5.89, 3.66, and 3.60, or
   b) 16.6, 15.7, 13.0, 10.7, 9.2, 8.7, 7.3, 6.0, 5.83, 5.39, 5.22, 3.92, 3.65, 3.53, 3.51, 3.44 and 3.40, or
   c) 10.8, 9.2, 3.93 and 3.66.

8. The crystalline material according to claim 1, wherein (b) is succinic acid, and the crystalline material has a powder X--ray diffraction pattern with the characteristic peaks expressed in d-values (Å): 21.1, 3.56, 3.45, and 3.36, or 10.3, 4.58, 3.52 and 3.35.

9. The crystalline material according to claim 1, wherein the carboxylic acid is gentisic acid, and the crystalline material has a powder X-ray diffraction pattern with the characteristic peaks expressed in d-values (Å):
   A) 16.2, 10.1, 3.45, 3.33, and 3.31, herein designated as nilotinib hydrochloride gentisic acid co-crystal form A;
   B) 16.1, 10.1, 7.3, 6.0, 5.60, 3.58, 3.42, 3.31, 3.28 and 3.25, herein designated as nilotinib hydrochloride gentisic acid co-crystal form B;
   C) 10.1, 7.7, 5.93, 5.02, 3.60, and 3.55, herein designated as nilotinib hydrochloride gentisic acid co-crystal form C;
   D) 16.3, 10.2, 6.1, 5.68, 3.62, 3.58, 3.46, 3.35, 3.32 and 3.29, herein designated as nilotinib hydrochloride gentisic acid co-crystal form D; or
   E) 16.2, 15.8, 9.9, 3.41, and 3.29, herein designated as nilotinib hydrochloride gentisic acid co-crystal form E.

10. The crystalline material according to claim 1, wherein the carboxylic acid is izentisic acid, and the crystalline material has a powder X-ray diffraction pattern with the characteristic peaks expressed in d-values (Å):
    16.2, 10.1, 7.4, 6.1, 5.59, 4.61, 3.61, 3.45, 3.33, 3.31 and 3.27, herein designated as nilotinib hydrochloride gentisic acid co-crystal form A; or
    16.2, 15.8, 9.9, 7.1, 5.97, 5.53, 4.76, 3.58, 3.53, 3.41, 3.29 and 3.23, herein designated as nilotinib hydrochloride gentisic acid co-crystal form E.

11. The crystalline material according to claim 1, wherein component (b) is a carboxylic acid amide or carboxylic acid ester, and wherein a molar ratio of component (a) and component (b) is from about 2:1 to about 1:1.

12. The crystalline material according to claim 1, wherein component (b) is isonicotinamide, and the crystalline material has a powder X-ray diffraction pattern with the characteristic peaks expressed in d-values (Å):
    13.6, 12.4, 6.2, 3.65, 3.54, 3.48 and 3.38, herein designated as the nilotinib hydrochloride isonicotinamide co-crystal.

13. The crystalline material according to claim 1, wherein component (b) is gallic acid methyl ester, and the crystalline material has a powder X-ray diffraction pattern with the characteristic peaks expressed in d-values (Å):
  17.2, 15.0, 12.3, 11.5, 8.0, 6.8, 5.66, 5.51 and 3.46, herein designated as the nilotinib hydrochloride gallic acid methyl ester co-crystal.

14. The crystalline material according to claim 1, wherein component (b) is 1,5-naphtalene disulfonic acid, and the crystalline material has a powder X-ray diffraction pattern with the characteristic peaks expressed in d-values (Å):
  a) 10.0, 9.4, 9.2, 7.7, 5.95, 4.83, 4.69, 3.53, 3.50, and 3.35, herein designated as nilotinib naphthalene disulfonic acid co-crystal form 1;
  b) 18.4, 9.9, 8.3, 7.8, 6.1, 5.86, 4.85, 4.63, 4.42, 4.29, 4.10, 3.87, and 3.68, herein designated as nilotinib naphthalene disulfbnic acid co-crystal form 2;
  c) 16.6, 5.78, 3.52, 3.46, and 3.40, herein designated as nilotinib naphthalene disulthnic acid co-crystal form 3;
  d) 12.0, 7.9, 6.8, 6.6, 5.50, 5.20, 4.74, 4.63, 3.76, 3.68, and 3.48, herein designated as nilotinib naphthalene disulfbnic acid co-crystal form 4;
  e) 12.0, 7.9, 7.7, 6.8, 6.0, 5.17, 4,72, 4.65, 3.72 and 3.51, herein designated as nilotinib naphthalene disulfonate form 5; or
  f) 12.0, 6.8, 5.20, 3.76 and 3.69, herein designated as nilotinib naphthalene disulfonate form 6.

15. The crystalline material according to claim 1, consisting essentially of
  (a) nilotinib, a hydrohalogenide salt of nilotinib, or a mixture of nilotinib and a hydrohalogenide salt of nilotinib;
  (b) fumaric acid, maleic acid, succinic acid, gentisic acid, isonicotinamide, gallic acid methyl ester, or 1,5-naphtalene disulfonic acid; and optionally
  (c) up to 2.5 mol of water per mol of nilotinib.

16. The crystalline material according to claim 1, wherein the crystalline material is suitable for the treatment of the human or animal body.

17. A pharmaceutical composition comprising a crystalline material according to claim 1, and optionally further comprising comprising pharmaceutically acceptable carriers, diluents, and/or further ingredients.

18. The pharmaceutical composition according to claim 17, wherein the pharmaceutical composition is suitable for the treatment of chronic myelogenous leukemia (CML).

19. The pharmaceutical composition according to claim 17, wherein the carboxylic acid is fumaric acid and which has at least one characteristic peak in an x-ray powder diffractogram expressed in d-values (Å) selected from 13.6, 7.1, 5.68, 4.84, 4.67, 4.57, 3.87, 3.69, 3.39, 3.36, 3.31, and 3.16; or
  wherein the carboxylic acid is maleic acid and which has at least one characteristic peak in an x-ray powder diffractogram expressed in d-values (Å) selected from 17.2, 15.8, 10.8, 9.1, 7.3, 5.89, 3.66, and 3.60; or
  wherein the carboxylic acid is maleic acid and which has at least one characteristic peak in an x-ray powder diffractogram expressed in d-values (Å) selected from 16.6, 15.7, 13.0, 10.7, 9.2, 8.7, 7.3, 6.0, 5.83, 5.39, 5.22, 3.92, 3.65, 3.53, 3.51, 3.44 and 3.40; or
  wherein the carboxylic acid is maleic acid and which has at least one characteristic peak in an x-ray powder diffractogram expressed in d-values (Å) selected from 10.8, 9.2, 5.4, 5.22, 3.93, 3.66, 3.54, 3.51, and 3.45; or
  wherein the carboxylic acid is succinic acid and which has at least one characteristic peak in an x-ray powder diffractogram expressed in d-values (Å) selected from 21.1, 3.56, 3.45, and 3.36, or 10.3, 4.58, 3.52 and 3.35; or
  wherein the carboxylic acid is gentisic acid and which has at least one characteristic peak in an x-ray powder diffractogram expressed in d-values (Å) selected from 16.2, 10.1, 3.45, 3.33, and 3.31; or
  wherein the carboxylic acid is gentisic acid and which has at least one characteristic peak in an x-ray powder diffractoaram expressed in d-values (Å) selected from 16.2, 15.8, 9.9, 3.41, and 3.29.

20. A process for preparing a crystalline material according to claim 1, comprising:
  (i) producing nilotinib,
    a hydrogen halide, and
    a carboxylic acid, carboxylic acid ester, carboxylic acid amide, or sulfonic acid; and
  (ii) mixing all the components produced in step (i) to obtain the crystalline material.

21. The crystalline material according to claim 1, wherein the carboxylic acid is maleic acid, and the crystalline material has a powder X-ray diffraction pattern with the following characteristic peaks expressed in d-values (Å): 10.8, 9.2, 5.4, 5.22, 3.93, 3.66, 3.54, 3.51, and 3.45.

* * * * *